US008202690B2

(12) United States Patent
Tatsumi et al.

(10) Patent No.: US 8,202,690 B2
(45) Date of Patent: Jun. 19, 2012

(54) CANCER MARKER AND THERAPEUTIC AGENT FOR CANCER

(75) Inventors: Yasutoshi Tatsumi, Chiba (JP); Akira Nakagawara, Chiba (JP)

(73) Assignees: Hisamitsu Pharmaceutical Co., Inc., Tosu-Shi (JP); Chiba-Prefecture, Chiba-Shi (JP)

( * ) Notice: Subject to any disclaimer, the term of this patent is extended or adjusted under 35 U.S.C. 154(b) by 0 days.

(21) Appl. No.: 12/626,346

(22) Filed: Nov. 25, 2009

(65) Prior Publication Data

US 2010/0136139 A1 Jun. 3, 2010

(30) Foreign Application Priority Data

Nov. 28, 2008 (JP) ................................ P2008-304897

(51) Int. Cl.
*C12Q 1/68* (2006.01)
(52) U.S. Cl. ....................................................... 435/6.1
(58) Field of Classification Search ............. 435/6, 91.1, 435/325, 375
See application file for complete search history.

(56) References Cited

U.S. PATENT DOCUMENTS

| 2005/0037389 A1* | 2/2005 | Santin ................................. 435/6 |
| 2005/0158792 A1 | 7/2005 | Bussemakers et al. |
| 2005/0272052 A1* | 12/2005 | Shekar et al. ...................... 435/6 |

FOREIGN PATENT DOCUMENTS

| EP | 1426443 A1 | 6/2004 |
| JP | 2003061672 A | 3/2003 |
| WO | 98/45420 A1 | 10/1998 |

OTHER PUBLICATIONS

Cavarretta et al: "Novel Experimental Therapeutic Approaches for Prostate Cancer" EAU Update Series, Elsevier LNKDDOI:10.1016/J. EUUS.2005.09.007, vol. 3, No. 4, Dec. 1, 2005, pp. 227-239, XP005215323.
Schalken Jack A et al: "New targets for therapy in prostate cancer: differential display code 3 (DD3(PCA3)), a highly prostate cancer-specific gene." Urology Nov. 2003 LNKD—Pubmed:14607216, vol. 62, No. 5 Suppl 1, Nov. 2003 pp. 34-43 XP002578236.
Clarke Raymond A et al: "New genomic structure for prostate cancer specific gene PCA3 within BMCC1: implications for prostate cancer detection and progression." Plos One 2009 LNKD-Pubmed:19319183, vol. 4, No. 3, 2009, p. E4995, XP002578237.
Thelen P et al: "Tectorigenin and other phytochemicals extracted from leopard lily Belamcanda chinensis affect new and established targets for therapies in prostate cancer" Carcinogenesis, Oxford University Press, GB LNKD-DOI:10.1093/CARCIN/BGI092, vol. 26 No. 8, Apr. 21, 2005, pp. 1360-1367, XP 002367976.
Machida, T. et al. "Increased expression of proapoptotic BMCC1, a novel gene with the BNIP2 and Cdc42GAP homology (BCH) domain, is associated with favorable prognosis in human neuroblastomas", Oncogene, 2006, vol. 25, p. 1931-p. 1942.

* cited by examiner

*Primary Examiner* — Christopher M. Babic
(74) *Attorney, Agent, or Firm* — Sughrue Mion, PLLC

(57) ABSTRACT

A novel cancer marker is provided. A method for detecting cancer using a level of BMCC1 gene expression as an indication is provided, in which the cancer is selected from the group consisting of prostate cancer, lung cancer, gastric cancer, bladder cancer, and uterine cancer.

2 Claims, 16 Drawing Sheets

Fig.7
(a)
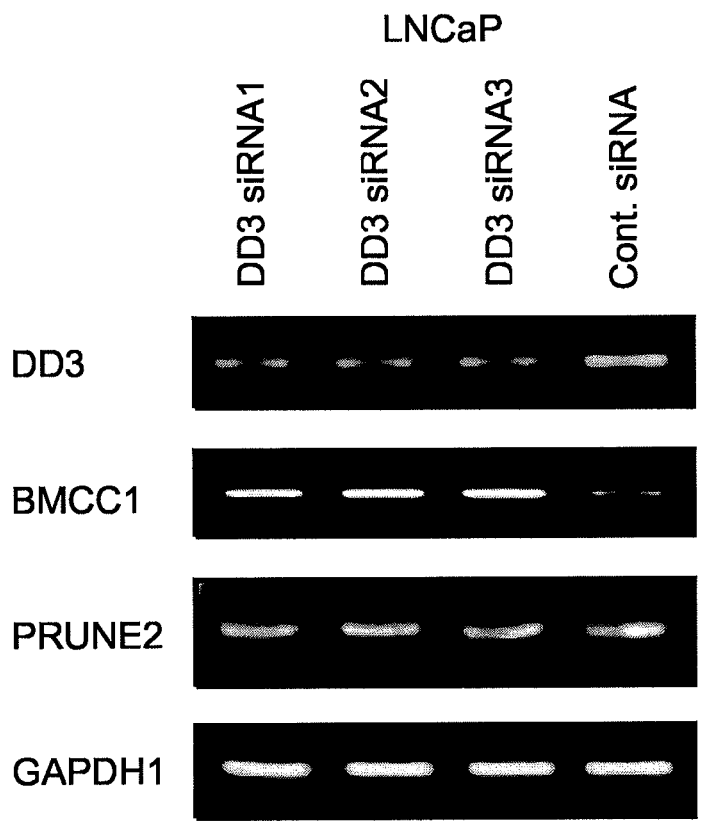
(b)
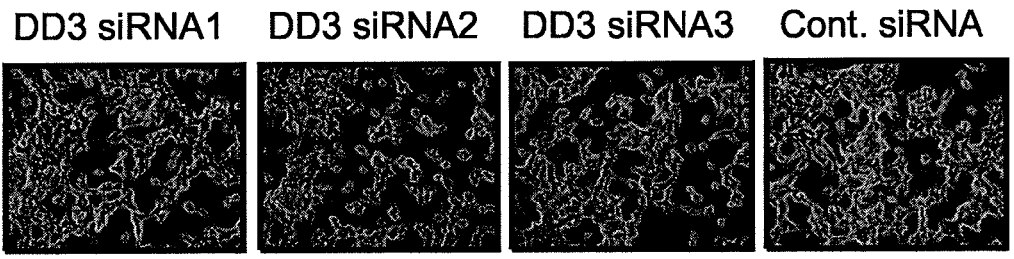

(semi-quantitative RT-PCR)

SEQUENCE LISTING

<160> NUMBER OF SEQ ID NOS: 35

<210> SEQ ID NO 1
<211> LENGTH: 31
<212> TYPE: DNA
<213> ORGANISM: Homo sapiens

<400> SEQUENCE: 1
ctgaacgatg aagggaaact gtcgataacg c              31

<210> SEQ ID NO 2
<211> LENGTH: 24
<212> TYPE: DNA
<213> ORGANISM: Homo sapiens

<400> SEQUENCE: 2
cactgcctgc cacggcttct gttg                      24

<210> SEQ ID NO 3
<211> LENGTH: 28
<212> TYPE: DNA
<213> ORGANISM: Homo sapiens

<400> SEQUENCE: 3
cacagcagat gttgaactcc aggtgttc                  28

<210> SEQ ID NO 4
<211> LENGTH: 22
<212> TYPE: DNA
<213> ORGANISM: Homo sapiens

<400> SEQUENCE: 4
ggtgggaagg acctgatgat ac                        22

<210> SEQ ID NO 5
<211> LENGTH: 23
<212> TYPE: DNA
<213> ORGANISM: Homo sapiens

<400> SEQUENCE: 5
gcacagggcg aggctcatcg atg                       23

<210> SEQ ID NO 6
<211> LENGTH: 20
<212> TYPE: DNA
<213> ORGANISM: Homo sapiens

<400> SEQUENCE: 6
accacagtcc atgccatcac                           20

<210> SEQ ID NO 7
<211> LENGTH: 20
<212> TYPE: DNA
<213> ORGANISM: Homo sapiens

<400> SEQUENCE: 7
tccaccaccc tgttgctgta                           20

<210> SEQ ID NO 8
<211> LENGTH: 20
<212> TYPE: DNA
<213> ORGANISM: Homo sapiens

<400> SEQUENCE: 8
gaagcctctg gtccagtcag    20

<210> SEQ ID NO 9
<211> LENGTH: 20
<212> TYPE: DNA
<213> ORGANISM: Homo sapiens

<400> SEQUENCE: 9
cttcggccgt atattctgga    20

<210> SEQ ID NO 10
<211> LENGTH: 19
<212> TYPE: DNA
<213> ORGANISM: Homo sapiens

<400> SEQUENCE: 10
tcctgcccat cctttaagg    19

<210> SEQ ID NO 11
<211> LENGTH: 25
<212> TYPE: RNA
<213> ORGANISM: Homo sapiens

<400> SEQUENCE: 11
ggaaccaaga uacaaagaac ucuga    25

<210> SEQ ID NO 12
<211> LENGTH: 27
<212> TYPE: RNA
<213> ORGANISM: Homo sapiens

<400> SEQUENCE: 12
ucagaguucu uuguaucuug guccuu    27

<210> SEQ ID NO 13
<211> LENGTH: 25
<212> TYPE: DNA
<213> ORGANISM: Homo sapiens

<400> SEQUENCE: 13
ucacuagaaa cagcaagaug acaat    25

<210> SEQ ID NO 14
<211> LENGTH: 27
<212> TYPE: RNA
<213> ORGANISM: Homo sapiens

<400> SEQUENCE: 14
auugucaucu ugcuguuucu agugaug    27

<210> SEQ ID NO 15
<211> LENGTH: 25
<212> TYPE: DNA
<213> ORGANISM: Homo sapiens

<400> SEQUENCE: 15
ggcauacuau aucaacuuug auuct    25

<210> SEQ ID NO 16
<211> LENGTH: 27
<212> TYPE: RNA
<213> ORGANISM: Homo sapiens

```
<400> SEQUENCE: 16
agaaucaaag uugauauagu augccaa                                27

<210> SEQ ID NO 17
<211> LENGTH: 25
<212> TYPE: RNA
<213> ORGANISM: Homo sapiens

<400> SEQUENCE: 17
cuuccucucu uucucucccu uguga                                  25

<210> SEQ ID NO 18
<211> LENGTH: 27
<212> TYPE: RNA
<213> ORGANISM: Homo sapiens

<400> SEQUENCE: 18
ucacaaggga gagaaagaga ggaagga                                27

<210> SEQ ID NO 19
<211> LENGTH: 22
<212> TYPE: DNA
<213> ORGANISM: Homo sapiens

<400> SEQUENCE: 19
ccagttcagt gctcagggtt ta                                     22

<210> SEQ ID NO 20
<211> LENGTH: 21
<212> TYPE: DNA
<213> ORGANISM: Homo sapiens

<400> SEQUENCE: 20
gcattcccac ccttacctca a                                      21

<210> SEQ ID NO 21
<211> LENGTH: 22
<212> TYPE: DNA
<213> ORGANISM: Homo sapiens

<400> SEQUENCE: 21
cacagagatc cctgggagaa at                                     22

<210> SEQ ID NO 22
<211> LENGTH: 22
<212> TYPE: DNA
<213> ORGANISM: Homo sapiens

<400> SEQUENCE: 22
ctgcccatcc tttaaggaac ac                                     22

<210> SEQ ID NO 23
<211> LENGTH: 20
<212> TYPE: PRT
<213> ORGANISM: Homo sapiens

<400> SEQUENCE: 23

Ala Lys Lys Pro Phe Ser Leu Lys Ala Asp Gly Glu Asn Pro Asp Ile
1               5                   10                  15

Leu Thr His Cys
            20

<210> SEQ ID NO 24
```

```
<211> LENGTH: 25
<212> TYPE: DNA
<213> ORGANISM: Homo sapiens

<400> SEQUENCE: 24
ggagaaggau auugacuuga agctg                                          25

<210> SEQ ID NO 25
<211> LENGTH: 28
<212> TYPE: RNA
<213> ORGANISM: Homo sapiens

<400> SEQUENCE: 25
cagcuucaag ucaauauccu uucuccau                                       28

<210> SEQ ID NO 26
<211> LENGTH: 25
<212> TYPE: DNA
<213> ORGANISM: Homo sapiens

<400> SEQUENCE: 26
ggaguaucag gaagcaaauc aggta                                          25

<210> SEQ ID NO 27
<211> LENGTH: 27
<212> TYPE: RNA
<213> ORGANISM: Homo sapiens

<400> SEQUENCE: 27
uaccugauuu gcuuccugau acuccaa                                        27

<210> SEQ ID NO 28
<211> LENGTH: 25
<212> TYPE: RNA
<213> ORGANISM: Homo sapiens

<400> SEQUENCE: 28
cccagugaga uaaacaauga agcag                                          25

<210> SEQ ID NO 29
<211> LENGTH: 27
<212> TYPE: RNA
<213> ORGANISM: Homo sapiens

<400> SEQUENCE: 29
cugcuucauu guuuaucuca cugggug                                        27

<210> SEQ ID NO 30
<211> LENGTH: 27
<212> TYPE: RNA
<213> ORGANISM: Homo sapiens

<400> SEQUENCE: 30
ggaguuagau uuaugcauau ugugguu                                        27

<210> SEQ ID NO 31
<211> LENGTH: 25
<212> TYPE: RNA
<213> ORGANISM: Homo sapiens

<400> SEQUENCE: 31
ccacaauaug cauaaaucua acucc                                          25

<210> SEQ ID NO 32
```

-continued

```
<211> LENGTH: 20
<212> TYPE: DNA
<213> ORGANISM: Homo sapiens

<400> SEQUENCE: 32
gcctctcgtg gcagggcagt                                              20

<210> SEQ ID NO 33
<211> LENGTH: 20
<212> TYPE: DNA
<213> ORGANISM: Homo sapiens

<400> SEQUENCE: 33
gggtgaactt gcgcacacac                                              20

<210> SEQ ID NO 34
<211> LENGTH: 25
<212> TYPE: DNA
<213> ORGANISM: Homo sapiens

<400> SEQUENCE: 34
tcaaaagagc cgctgaaggg aaaca                                        25

<210> SEQ ID NO 35
<211> LENGTH: 25
<212> TYPE: DNA
<213> ORGANISM: Homo sapiens

<400> SEQUENCE: 35
acaccatgag ccccatccag gagta                                        25
```

CANCER MARKER AND THERAPEUTIC AGENT FOR CANCER

BACKGROUND OF THE INVENTION

1. Field of the Invention

The present invention relates to a cancer marker and a therapeutic agent for cancer.

2. Related Background Art

Prostate cancer is the cancer which has the highest prevalence among males in Europe and the U.S. Also in Japan, the number of patients with prostate cancer is increasing year by year along with westernization of dietary habits and aging of the population. Prostate cancer includes an androgen-dependent tumor and an androgen-independent tumor. Generally, proliferation of prostate cancer cells is stimulated by androgen; therefore, in treatment of unresectable progressive prostate cancer, androgen blockade therapy, which inhibits production and function of androgen, is frequently implemented. Early-stage prostate cancer often responds to androgen blockade therapy because most of it is androgen dependent. However, once it has progressed to an androgen-independent tumor, androgen blockade therapy cannot be implemented, and even more, no good treatment method exists. In view of the foregoing, effective treatment for androgen-independent tumor is needed.

A BMCC1 gene is a novel gene discovered as a result of a research project "a comprehensive gene expression analysis in tumor tissue using a cDNA microarray derived from a tumor of neuroblastoma and identification of a cancer suppressor gene, an oncogene, and a prognosis-determining factor using the same" in Chiba Cancer Center, by which a strong correlation between BMCC1 gene expression and prognosis of neuroblastoma was reported (Patent Document 1 and Non-Patent Document 1). However, involvement of the BMCC1 gene in prostate cancer is not known.

Patent Document 1: Japanese Patent Laid-Open No. 2003-061672

Non-Patent Document 1: Machida, T. et al., (2006), Oncogene, Vol. 25, p 1931-1942

If molecular mechanisms of a gene involved in cancer are elucidated and a therapeutic medicine based on a novel mechanism can be developed, a range of options for cancer diagnosis and cancer treatment can be expanded. Accordingly, an object of the present invention is to provide a novel cancer marker. Another object of the present invention is to provide a novel therapeutic agent for cancer.

SUMMARY OF THE INVENTION

The present inventors found that the BMCC1 gene was expressed in tissues other than neural tissue in which expression of the gene had been previously known, and BMCC1 gene expression in prostate cancer, lung cancer, gastric cancer, bladder cancer, and uterine cancer was reduced compared with a normal specimen based on experimental results of an expression analysis of cancer tissue. The present inventors further found that BMCC1 gene expression was enhanced when DD3 expression was suppressed by DD3-specific siRNA. Combined with the findings that DD3 expression is enhanced in early-stage prostate cancer, while BMCC1 expression is suppressed in late-stage prostate cancer, the aforementioned findings suggest a possibility that DD3 inhibits BMCC1 gene expression and promotes cancer progression. The present inventors completed the present invention based on the findings as described above.

That is to say, the present invention provides a method for detecting cancer using a level of BMCC1 gene expression as an indication, in which the cancer is selected from the group consisting of prostate cancer, lung cancer, gastric cancer, bladder cancer, and uterine cancer. Among them, the cancer is preferably prostate cancer.

Furthermore, the method for detecting cancer according to the present invention is characterized by including a step of measuring a level of BMCC1 gene expression in a specimen with a suspicion of cancer, a step of comparing the level of BMCC1 gene expression with levels of BMCC1 gene expression in a normal specimen and in a cancer specimen, and a step of judging the specimen suspect of being affected by cancer as cancer in a case where the level of BMCC1 gene expression in the specimen with a suspicion of cancer is (i) lower than the level of BMCC1 gene expression in the normal specimen, (ii) the same level as the level of BMCC1 gene expression in the cancer specimen, or falls into both (i) and (ii). The specimen is preferably a cell or a piece of tissue.

The method for detecting cancer according to the present invention is based on findings discovered by the inventors of the present application that the BMCC1 gene is expressed in tissues other than neural tissue in which expression of the gene has been previously known, and BMCC1 gene expression in prostate cancer, lung cancer, gastric cancer, bladder cancer, and uterine cancer is reduced compared with a normal tissue. Provision of a cancer marker for a method for detecting cancer is made possible by the above findings.

The present invention provides siRNA which targets DD3, in which the siRNA is double-stranded siRNA comprising a pair of oligonucleotides of any one of (a) to (d) as described below;

(a) an oligonucleotide comprising a sequence described in SEQ ID NO: 11 and an oligonucleotide comprising a sequence described in SEQ ID NO: 12;

(b) an oligonucleotide comprising a sequence described in SEQ ID NO: 13 and an oligonucleotide comprising a sequence described in SEQ ID NO: 14;

(c) an oligonucleotide comprising a sequence described in SEQ ID NO: 15 and an oligonucleotide comprising a sequence described in SEQ ID NO: 16; and (d) an oligonucleotide comprising a sequence described in SEQ ID NO: 30 and an oligonucleotide comprising a sequence described in SEQ ID NO: 31.

The present invention further provides a therapeutic agent for cancer containing the siRNA described above as an active ingredient. The cancer described above is preferably selected from the group consisting of prostate cancer, lung cancer, gastric cancer, bladder cancer, and uterine cancer, among which it is more preferably prostate cancer.

DD3 is a non-coding RNA which is known as a prostate cancer marker. DD3 is encoded by q21.13 of chromosome 9, and interestingly, it is inserted in reverse orientation in intron 6 of the BMCC1 gene (FIG. 1), based on which the inventors of the present application established a hypothesis that DD3 suppressively regulates BMCC1 gene expression. The hypothesis was examined in Examples of the present application. In fact, the inventors of the present application found for the first time that BMCC1 gene expression was enhanced and viability of cancer cells is more effectively suppressed by suppression of DD3 expression by DD3-specific siRNA. The present invention is based on the above-described findings, and delay in cancer progression and improvements in symptoms of cancer can be expected by a therapeutic agent of the present invention.

The present invention provides a therapeutic agent for cancer, which further contains an anti-cancer agent. The anti-cancer agent is preferably cisplatin. Also, the present invention provides a therapeutic agent for cancer, which further contains an anti-androgen agent. The cancer is preferably prostate cancer.

The present invention is based on a finding that viability of cancer cells is more effectively suppressed when treatment with cisplatin and/or removal of androgen are/is employed concurrently in addition to inhibition of DD3 expression, and delay in cancer progression, improvements in symptoms of cancer, and the like can be expected by the therapeutic agent of the present invention.

BRIEF DESCRIPTION OF THE DRAWINGS

FIG. 7(A) shows the results of expression of BMCC1 gene, PRUNE2 gene, and DD3 gene in an LNCaP cell line into which siRNA for DD3 was introduced as examined by semi-quantitative RT-PCR, and (B) shows cells 48 hours after introduction of siRNA;

DESCRIPTION OF THE PREFERRED EMBODIMENTS

Preferred embodiments of the present invention are described in detail hereinbelow.

BMCC1 gene and DD3

Figure 1:
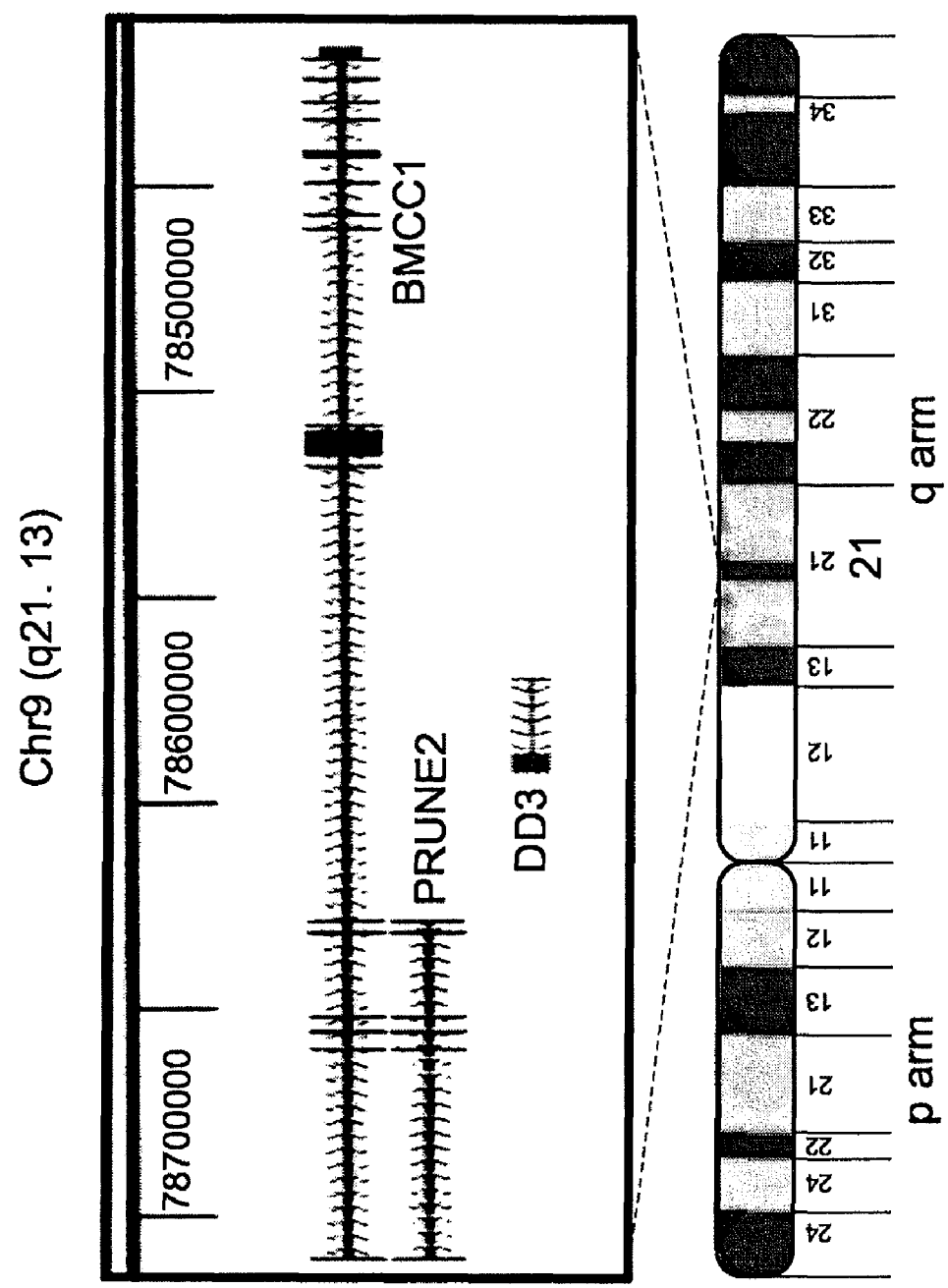
FIG. 1 schematically shows chromosomal locations of human BMCC1 gene, PRUNE2 gene, and DD3 gene.

The BMCC1 gene, which stands for BCH motif-containing molecule at the carboxyl terminal region 1, is a gene identified by the inventors of the present application as a gene involved in determination of prognosis of neuroblastoma in Japanese Patent Laid-Open No. 2003-061672 and Machida, T. et al., (2006), Oncogene, Vol. 25, p 1931-1942. GenBank Accession No. of the gene is AB050197. BMCC1 protein is 340 kDa in size, and has Bcl2/Adenovirus E1B 19 kDa interacting protein 2 (i.e., BNIP2) and Cdc42GAP homology domain (i.e., BCH domain) in a C terminal side thereof. FIG. 1 schematically shows chromosomal locations of human BMCC1 gene, PRUNE2 gene, and DD3 gene. As shown in FIG. 1, the BMCC1 gene locates in q21.13 of human chromosome 9. Also, in the same chromosomal region, a PRUNE 2 gene is present (GenBank Accession No. NM138818). Further, it was found that the DD3 gene was inserted in reverse orientation in intron 6 of the BMCC1 gene. Namely, a sequence of the DD3 gene was perfectly complementary to a part of intron 6 of the BMCC1 gene. DD3 encoded by the DD3 gene (GenBank Accession No. AF103907) is a non-coding RNA (i.e., ncRNA), which is also called a prostate cancer antigen (i.e., PCA). It is known as a prostate cancer marker; however, involvement of DD3 in a mechanism of tumorigenesis has not been elucidated.

Based on the findings that the sequence of DD3 gene is complementary to the sequence of BMCC1 gene and that BMCC1 gene expression and DD3 expression had a tendency toward an inverse correlation as suggested by the results from Examples 1 and 2 as shown below, the present inventors proposed a hypothesis that an inhibitory mechanism of BMCC1 expression by DD3 existed as an inhibitory mechanism of BMCC1 function. Findings supportive of the hypothesis were obtained by Examples 3-6 as shown below. Namely, because BMCC1 gene expression was enhanced by suppression of DD3 expression, it was strongly suggested that DD3 suppressively regulated BMCC1 gene expression. Also, it was elucidated that BMCC1 gene expression could be enhanced and viability of cancer cells could be suppressed by suppression of DD3 expression.

Most of the early-stage prostate cancer is androgen dependent so that it is often cured with androgen blockade therapy. However, prostate cancer recurred thereafter cannot be treated with androgen blockade therapy, and even more, no good treatment method exists. A fact that a number of androgen-dependent prostate cancer is cured with androgen blockade therapy suggests that a gene cluster induced by androgen is involved in oncogenic transformation of the prostate gland. Findings that DD3 expression is enhanced in the early-stage prostate cancer and BMCC1 expression is inhibited in the late-stage prostate cancer, which were elucidated for the first time by the present invention, suggest a possibility that DD3 inhibits BMCC1 gene expression and promotes cancer progression. Accordingly, if BMCC1 gene expression is enhanced by specifically suppressing DD3 expression, an effect is expected from the standpoint of cancer treatment and delay in cancer progression. Furthermore, as shown in Examples 7 and 8 below, it has been found that viability of cancer cells can be more effectively suppressed when treatment with cisplatin and/or removal of androgen are/is employed concurrently in addition to suppression of DD3 expression. Accordingly, it was suggested that combination use of the therapeutic agent of the present invention and another treatment method which employs an anti-cancer agent, an anti-androgen agent, and the like was effective.

Method for Detecting Cancer

A method for detecting cancer according to the present embodiment is described. The method for detecting cancer according to the present embodiment is based on a level of BMCC1 gene expression as an indication. Using the BMCC1 gene as a cancer marker, the method detects a cancer cell or cancer tissue based on the finding of the present invention that there is a correlation between a low level of BMCC1 gene expression and cancer. Furthermore, the method for detecting cancer according to the present embodiment includes a step of measuring a level of BMCC1 gene expression in a specimen with a suspicion of cancer, a step of comparing the level of BMCC1 gene expression with levels of BMCC1 gene expression in a normal specimen and in a cancer specimen, and a step of judging the specimen suspect of being affected by cancer as cancer in a case where the level of BMCC1 gene expression in the specimen with a suspicion of cancer is (i) lower than BMCC1 gene expression in the normal specimen, (ii) the same level as the level of BMCC1 gene expression in the cancer specimen, or falls into both (i) and (ii).

A preferred subject can be a human. The cancer is preferably selected from the group consisting of prostate cancer, lung cancer, gastric cancer, bladder cancer, and uterine cancer, among which it is more preferably prostate cancer. The specimen is preferably a cell or a piece of tissue which is susceptible to onset of cancer to be examined.

A level of gene expression refers to a level of mRNA expression, which is a transcription product of the gene, and/or a level of protein expression, which is a translation product of the mRNA. A level of mRNA expression can be measured by a measurement system publicly known to a person skilled in the art, and specific examples thereof include a semi-quantitative RT-PCR method, a quantitative real-time RT-PCR method, a quantitative Northern blotting method, and a quantitative ribonuclease protection method. A level of protein expression can be measured by a measurement system publicly known to a person skilled in the art, and examples thereof include a quantitative Western blotting method and an ELISA method. Using levels of mRNA and/or protein expression of GAPDH, which is a housekeeping gene, beta-actin, and the like as a control, the level of expression of an objective gene such as a BMCC1 gene is standardized. Also, levels of objective gene expression and/or control gene expression in an aliquot derived from a plurality of samples and/or an identical sample obtained from an identical subject are measured, and the level of expression can be obtained from a mean value of each of them. Gene expression can be quantitatively measured by using these methods.

Primers and probes for detecting BMCC1 mRNA can be designed by a method commonly known to a person skilled in the art. As for primers for detecting BMCC1 mRNA, a BMCC1 (BNF2/BNR2) primer set (SEQ ID NOS: 1 and 2), a kiaa0367F/R primer set (SEQ ID NOS: 8 and 9), and the like are exemplified; however, the primers are not limited to these examples. Also, an antibody, an antibody fragment, and the like for detecting BMCC1 protein can be prepared by a method commonly known to a person skilled in the art. As for a usable anti-BMCC1 antibody, an antibody raised against an epitope containing residues from 2074 to 2093 of BMCC1 protein (i.e., amino acid sequence: AKKPFSLKADGENP-DILTHC, as shown by single-letter codes of amino acids; SEQ ID NO: 23), an antibody raised against an epitope containing residues from 3068 to 3088 of BMCC1 protein (i.e., amino acid sequence: YNDPEMSSMEKDIDLKLKEKP, as shown by single-letter codes of amino acids), an antibody raised against an epitope containing residues from 1733 to 1753 of BMCC1 protein (i.e., amino acid sequence: KSENIYDYLDSSEPAENENKSNPFC, as shown by single-letter codes of amino acids), a commercially available antibody, and the like are preferably used; however, the antibody is not limited to these examples.

The level of BMCC1 gene expression in a normal specimen can be obtained by statistically processing a measurement value of a level of expression which is obtained from a specimen derived from a plurality of normal tissue which are not oncogenically transformed obtained from single or a plurality of subject(s) (a control group). Also, the level of BMCC1 gene expression in a cancer specimen can be obtained by statistically processing measurement values of a level of expression obtained from specimens derived from a plurality of cancer tissues obtained from single or a plurality of patient(s) of cancer (a disease group). As for detection of cancer, specifically, (i) a specimen with a suspicion of cancer is judged as a cancer specimen in a case where the level of BMCC1 gene expression in the specimen with a suspicion of cancer is lower than the level of BMCC1 gene expression in the normal specimen, and/or in a case where, in comparison with the level of expression obtained from the control group, the level of BMCC1 gene expression statistically corresponds to a range lower than a distribution range of the control group. Also, (ii) a specimen with a suspicion of cancer is judged as a cancer specimen in a case where the level of BMCC1 gene expression in the specimen with a suspicion of cancer is the same level as the level of BMCC1 gene expression in the cancer specimen, and/or in a case where, in comparison with the level of expression obtained from the disease group, the level of BMCC1 gene expression statistically corresponds to a distribution range of the disease group. Furthermore, a specimen with a suspicion of cancer is judged as a cancer specimen in a case where the level of BMCC1 gene expression in the specimen with a suspicion of cancer falls into both (i) and (ii).

Therapeutic Agent for Cancer

The siRNA which targets DD3 according to the present embodiment is double-stranded siRNA comprising a pair of oligonucleotides of any one of (a) to (d) as described below;
(a) an oligonucleotide comprising a sequence described in SEQ ID NO: 11 and an oligonucleotide comprising a sequence described in SEQ ID NO: 12;
(b) an oligonucleotide comprising a sequence described in SEQ ID NO: 13 and an oligonucleotide comprising a sequence described in SEQ ID NO: 14;
(c) an oligonucleotide comprising a sequence described in SEQ ID NO: 15 and an oligonucleotide comprising a sequence described in SEQ ID NO: 16; and
(d) an oligonucleotide comprising a sequence described in SEQ ID NO: 30 and an oligonucleotide comprising a sequence described in SEQ ID NO: 31.

The term siRNA is an abbreviation for short interfering RNA, and refers to a double-stranded RNA having 10 or more base pairs which is obtained by artificial chemical synthesis or biochemical synthesis, or by synthesis inside a body of an organism, or by degradation of double-stranded RNA having approximately 40 or more bases inside a body. A length of siRNA is generally 10-30-base long, preferably approximately 15-25-base long, more preferably around 19-23-base long. The siRNA usually has a structure of 5'-phosphate and 3'-OH, and approximately 2 bases overhang at the 3'-end thereof.

Administration of siRNA to a cell can specifically inhibit DD3 expression by an RNA interference effect. That is, when siRNA is introduced inside a cell, protein specific to the siRNA binds thereto to form a RISC (i.e., RNA-induced-silencing-complex). The complex recognizes and binds to mRNA having a sequence identical to the siRNA, and cleaves the mRNA at a center of the siRNA by an RNase III-like enzymatic activity. As described above, siRNA can inhibit expression of a target gene (i.e., DD3 gene in the present invention) by degrading mRNA having a sequence homologous to the siRNA. A phenomenon described above is called RNA interference (RNAi). The RNAi phenomenon is a phenomenon observed in nematodes, insects, protozoa, hydras, plants, and vertebrates (including mammals).

Also, in another embodiment, siRNA specific to DD3 other than the ones described above can be used. Furthermore, shRNA (i.e., short hairpin RNA) and dsRNA (i.e., double strand RNA) capable of producing the siRNA, or an expression vector which can express the shRNA and the dsRNA can be employed. When the shRNA, the dsRNA, or the expression vector thereof is administered to a cell, siRNA is produced inside the cell. A promoter of an RNA polymerase III (Pol III) which participates in a transcription system of U6RNA or H1RNA can be used as a promoter for the expression vector of the RNA.

Further, in another embodiment, the siRNA described above can be RNA, RNA: DNA hybrid, or a modified nucleic acid (RNA and DNA). Specific examples of the modified nucleic acid(s) can be sulfur derivatives and thiophosphate derivatives of nucleic acid(s), as well as ones resistant to degradation of polynucleotide amide and oligonucleotide amide; however, the modified nucleic acid(s) are not limited to these examples.

The therapeutic agent for cancer according to the present embodiment has the siRNA described above as an active ingredient. The therapeutic agent for cancer can contain the siRNA singly or 2 or more thereof in combination.

In a preparation of the therapeutic agent for cancer according to the present invention, a pharmaceutically acceptable carrier can be added as needed in accordance with a conventional method. For example, it can be a surfactant, an excipient, a colorant, a scent, a preservative, a stabilizer, a buffer, a suspending agent, a tonicity agent, a binder, a disintegrant, a lubricant, a fluidity promoter, and a flavor; however, it is not limited to these examples, and a carrier which is ordinarily used can be employed as appropriate. Specific examples thereof can be light anhydrous silicic acid, lactose, crystalline cellulose, mannitol, starch, carmellose calcium, carmellose sodium, hydroxypropyl cellulose, hydroxypropylmethyl cellulose, polyvinyl acetal diethylaminoacetate, polyvinylpyrrolidone, gelatin, medium-chain fatty acid triglyceride, polyoxyethylene hardened castor oil 60, sucrose, carboxymethylcellulose, corn starch, an inorganic salt, and the like.

Kinds of formulation of the therapeutic agent for cancer according to the present invention can be, for example, an oral agent such as a tablet, a pulverized agent, a pill, a powder, a granule, a fine granule, soft and hard capsules, a film-coated preparation, a pellet, a sublingual agent, and a paste, as well as a parenteral agent such as an injection, a suppository, a percutaneous agent, an ointment, a plaster, and a liquid preparation for external use, and a person skilled in the art can select a most suitable dosage form according to an administration route, a subject to be administered, and the like. A prepared product can contain 0.1 to 99.9% by weight of the siRNA described above as an active ingredient.

Although a dose of the active ingredient of the therapeutic agent for cancer according to the present invention differs depending on a subject to be administered, a target organ, a symptom, a method of administration, and the like, a daily dose is generally, for example, approximately 0.1 mg to 1,000 mg, preferably approximately 1.0 to 100 mg, more preferably approximately 1.0 to 50 mg for a patient (supposed to weigh 60 kg) in a case of oral administration. In a case of parenteral administration, although a dose per administration differs depending on a subject to be administered, a target organ, a symptom, a method of administration, and the like, for example, it is convenient in a case of an injection, generally, for example, to administer at approximately 0.01 to around 30 mg, preferably at approximately 0.1 to around 20 mg, more preferably at approximately 0.1 to around 10 mg daily to a patient (supposed to weigh 60 kg) by an intravenous injection. However, the dose can ultimately be determined as appropriate based on judgment of a physician in consideration of a kind of dosage form, an administration method, age and weight of a patient, a patient's symptoms, and the like.

The therapeutic agent for cancer according to the present invention is used for prevention and treatment of prostate cancer, lung cancer, gastric cancer, bladder cancer, uterine cancer, and the like, and it is preferably used for prevention and treatment of prostate cancer.

In another embodiment, the therapeutic agent for cancer according to the present invention can be used in combination with an anti-cancer agent. The anti-cancer agent can be cisplatin, peplomycin, ifosfamide, tegafur/uracil, estramustine, docetaxel, gemcitabine, oxaliplatin, and the like, among which it is preferably cisplatin. Also, in another embodiment, the therapeutic agent for cancer according to the present invention can be used in combination with an anti-androgen agent. Furthermore, in another embodiment, the therapeutic agent for cancer according to the present invention can be used in combination with an anti-cancer agent and an anti-androgen agent.

EXAMPLES

Preferred Examples of the present invention are described further in detail hereinbelow; however, the present invention is not limited to these Examples.

Example 1

An Expression Analysis of BMCC1 Gene, PRUNE2 Gene, and DD3 Gene in Human Normal Tissue Using a total RNA extracted from human normal tissue (product of Clontech Laboratories, Inc.), a semiquantitative RT-PCR was conducted following the below-described experimental procedures to examine mRNA expression of BMCC1 gene, PRUNE2 gene, and DD3 gene.

1-1) cDNA Synthesis

Using SuperScript First-Strand Synthesis System for RT-PCR (product of Invitrogen Corporation), cDNA was synthesized following a protocol of the product. For cDNA synthesis, 2 μg of the total RNA and random primers (Random Hexamers, product of Invitrogen Corporation) were used.

1-2) PCR Reaction

A PCR reaction was carried out with the following conditions.

<Primers>

BMCC1;
(SEQ ID NO: 1)
BNF2:    5'-ctgaacgatgaagggaaactgtcgataacgc-3'
and

```
                                                    (SEQ ID NO: 2)
BNR2:       5'-cactgcctgccacggcttctgttg-3'

PRUNE2;
                                                    (SEQ ID NO: 1)
BNF2
and
                                                    (SEQ ID NO: 3)
PRUNE2R1:   5'-cacagcagatgttgaactccaggtgttc-3'

DD3;
                                                    (SEQ ID NO: 4)
DD3F3:      5'-ggtgggaaggacctgatgatac-3'
and
                                                    (SEQ ID NO: 5)
DD3R3:      5'-gcacagggcgaggctcatcgatg-3'

GAPDH1;
                                                    (SEQ ID NO: 6)
GAPDH1F:    5'-accacagtccatgccatcac-3'

(SEQ ID NO: 7)
GAPDH1R:    5'-tccaccaccctgttgctgta-3'
```

<A Composition of Reaction Solution>

| | |
|---|---|
| cDNA | 1 μl |
| 10x rTaq Buffer | 1 μl |
| 2.5 mM dNTPs | 1 μl |
| Forward primers (10 μM) | 0.5 μl |
| Reverse primers (10 μM) | 0.5 μl |
| Sterilized water | 6 μl |
| rTaq | 0.1 μl |
| Total volume | 10 μl |

<Reaction Conditions>

A tube containing a reaction solution of the above composition was set in a thermal cycler (Gene Amp® PCR System 9700, product of Applied Biosystems). In a case of a BMCC1 (BNF2/BNR2) primer set (SEQ ID NOS: 1 and 2), a sample was heated to 95° C. for 2 minutes, after which a cycle containing 95° C. for 15 seconds→59° C. for 15 seconds→72° C. for 20 seconds was repeated 38 times, and the sample was kept at 72° C. for 6 minutes. In a case of a PRUNE2 (BNF2/PRUNE2R1) primer set (SEQ ID NOS: 1 and 3), a sample was heated to 95° C. for 2 minutes, after which a cycle containing 95° C. for 15 seconds→59° C. for 15 seconds→72° C. for 20 seconds was repeated 38 times, and the sample was kept at 72° C. for 7 minutes. In a case of a DD3 (F3/R3) primer set (SEQ ID NOS: 4 and 5), a sample was heated to 95° C. for 2 minutes, after which a cycle containing 95° C. for 15 seconds→63° C. for 15 seconds→72° C. for 20 seconds was repeated 38 times, and the sample was kept at 72° C. for 6 minutes. In a case of a GAPDH 1 (F1/R1) primer set (SEQ ID NOS: 6 and 7), a sample was heated to 95° C. for 2 minutes, after which a cycle containing 95° C. for 15 seconds→58° C. for 15 seconds→72° C. for 20 seconds was repeated 28 times, and the sample was kept at 72° C. for 6 minutes. The PCR products thus obtained were subjected to electrophoresis on 2% agarose gel and detected by ethidium bromide (product of SIGMA Corporation).

Figure 2:
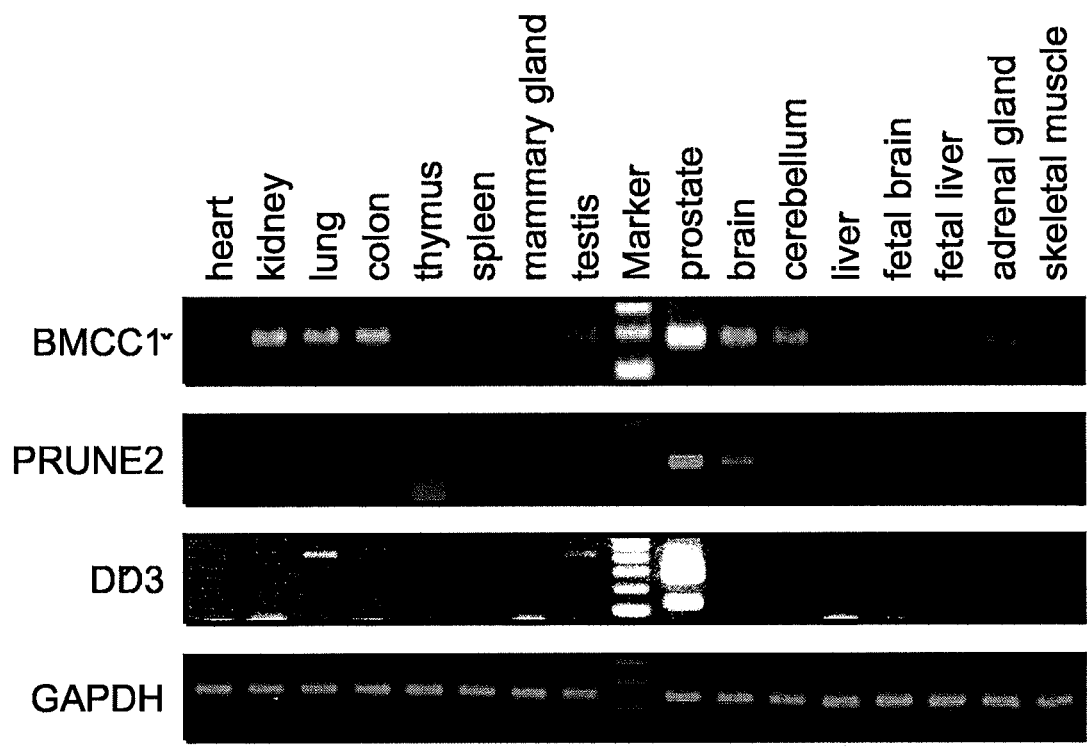
FIG. 2 shows the results of expression of BMCC1 gene, PRUNE2 gene, and DD3 gene in human normal tissue as examined by semiquantitative RT-PCR.

The results of BMCC1 gene, PRUNE2 gene, and DD3 gene expression in human normal tissue as examined by a semiquantitative RT-PCR are shown in FIG. 2. As a result, BMCC1 expression was confirmed in tissues other than the neural system in which BMCC1 expression had been reported. Also, DD3 was expressed prominently in the prostate gland.

Example 2

An Expression Analysis of BMCC1 Gene and DD3 Gene in a Matched Pair of Human Normal Tissue and Cancer Tissue In view of the foregoing, BMCC1 expression in various cancer was examined using a matched pair of normal tissue and cancer tissue derived from patients of lung cancer (2 patients), gastric cancer (2 patients), bladder cancer (4 patients), uterine cancer (1 patient), and prostate cancer (2 patients) by an RT-PCR method.

The method described in Example 1 was employed except that a total RNA extracted from a matched pair of human normal tissue and cancer tissue (product of Clontech Laboratories, Inc.) was used and a kiaa0367F/R primer set (SEQ ID NOS: 8 and 9) was used in addition to a BNF2/BNR2 primer set (SEQ ID NOS: 1 and 2) as a primer for detecting BMCC1.

<BMCC1 (kiaa0367F/R) Primers and PCR Reaction Conditions>

```
BMCC1;
kiaa0367F:
5'-gaagcctctggtccagtcag-3'      (SEQ ID NO: 8)
and kiaa0367R:
5'-cttcggccgtatattctgga-3'      (SEQ ID NO: 9)
```

A PCR reaction using a BMCC1 (kiaa0367F/R) primer set was carried out by heating the sample to 95° C. for 2 minutes and repeating a cycle containing 95° C. for 15 seconds→61° C. for 15 seconds→72° C. for 20 seconds 35 times, followed by keeping the sample at 72° C. for 6 minutes.

Figure 3:
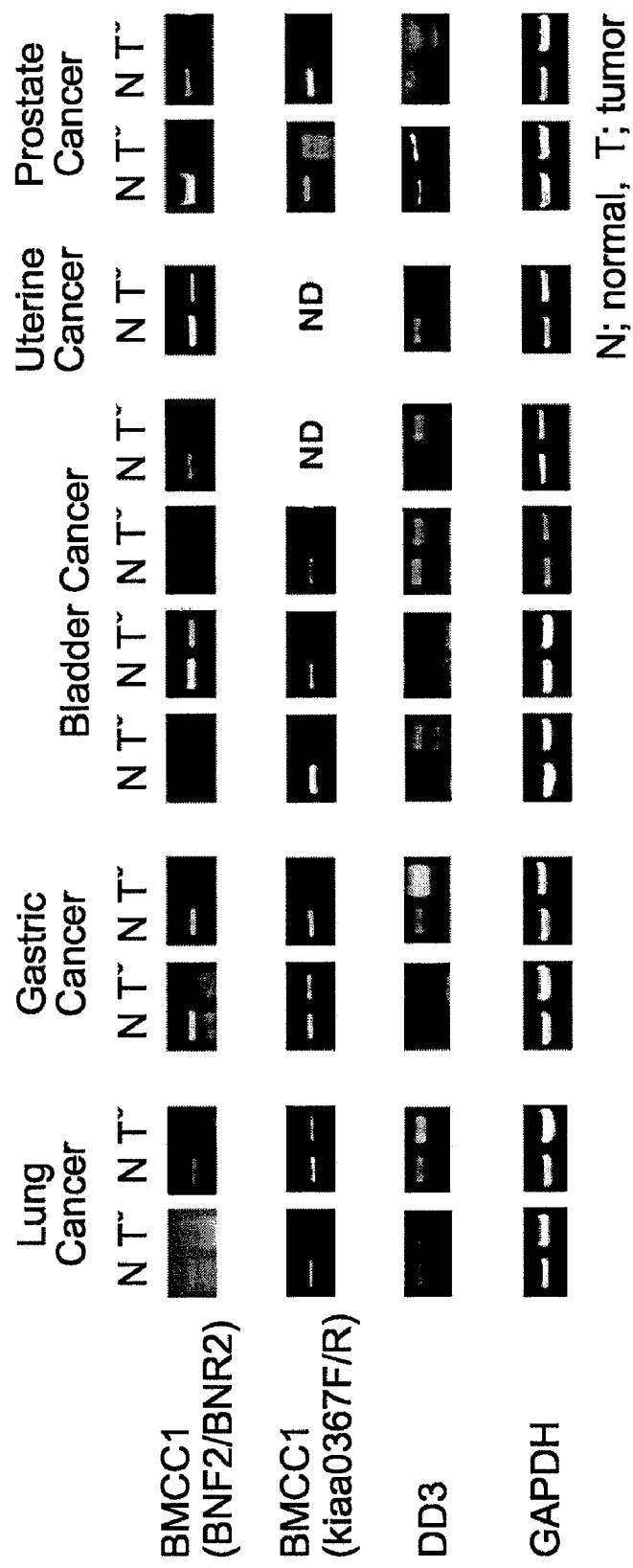
FIG. 3 shows the results of expression of BMCC1 gene and DD3 gene in a matched pair of human normal tissue and cancer tissue as examined by semiquantitative RT-PCR, in which N means a sample derived from normal tissue, T means a sample derived from tumor cell tissue, and ND means Not Determined.

The results of expression of BMCC1 gene and DD3 gene in the matched pair of human normal tissue and cancer tissue as examined by a semiquantitative RT-PCR are shown in FIG. 3. As a result, BMCC1 expression was found to be reduced in a cancer site compared with a normal site, which suggested that a functional inhibition of BMCC1 in cancer was caused by reduction in its expression. Also, it was found that DD3 expression was enhanced in a plurality of cancer tissues.

Example 3

An Expression Analysis of BMCC1 Gene, PRUNE2 Gene, and DD3 Gene in a Prostate Cancer Cell Line To verify a possibility that DD3 suppressively regulates BMCC1 gene expression, expression of BMCC1 gene, PRUNE2 gene, and DD3 gene was confirmed in a cell line established from prostate cancer according to the following method.

An LNCaP cell line, a PC3 cell line, and a Du145 cell line, all of which were cell lines established from prostate cancer, were provided by Dr. Ueda (Director of Department of Urology, Chiba Cancer Center) and used in this examination. The LNCaP cell is an androgen dependent cell line, while the PC3 cell and the Du145 cell are androgen independent cell lines. Properties of these cell lines are shown in Table 1. Also, a SK-N-BE cell line, which was a neuroblastoma cell line, was used as a control.

TABLE 1

| Cell line | Androgen sensitivity | DD3 mRNA | TP53* Status |
|---|---|---|---|
| LNCaP | Androgen dependent (Androgen sensitive) | Positive | Wild type |
| PC3 | Androgen independent | Negative | Mutant (138 frameshift 169 stop codon) |
| Du145 | Androgen independent | Negative | Mutant (P223L) |

*TP53: tumor protein p53 (GENEBANK ACCESSION No. NM000546)

Cultured cells of each cell line (80% confluent in a 100 mm dish) were collected and suspended in 1 mL of ISOGEN (product of Nippon Gene Co., Ltd.), from which a total RNA was purified following a protocol of the product. The methods described in Example 1 were employed for cDNA synthesis and PCR reactions except that a F3/R primer set (SEQ ID NOS: 4 and 10) was used in addition to a F3/R3 primer set (SEQ ID NOS: 4 and 5) as a primer for detecting DD3.

<DD3 (F3/R) Primers and PCR Reaction Conditions>

```
DD3;
F3                                        (SEQ ID NO: 4)
and

DD3R:   5'-tcctgcccatcctttaagg-3'         (SEQ ID NO: 10)
```

A PCR reaction using a DD3 (F3/R) primer set was carried out by heating the sample to 96° C. for 5 minutes and repeating a cycle containing 96° C. for 30 seconds→62° C. for 60 seconds 35 times.

Figure 4:
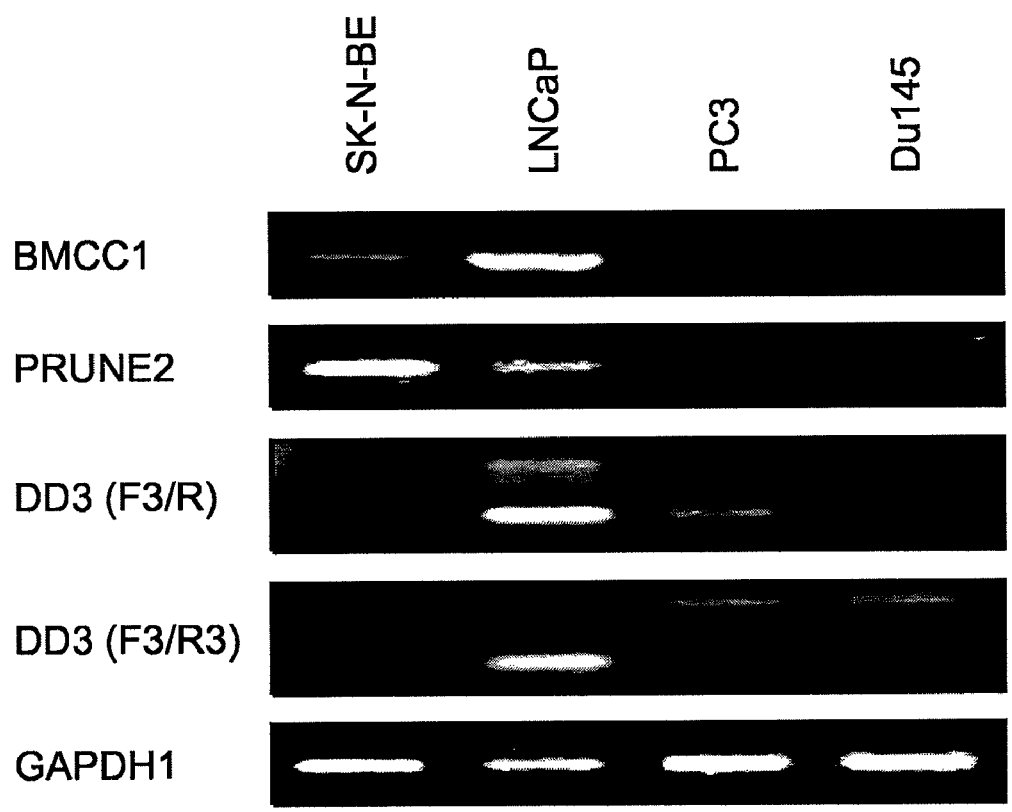
FIG. 4 shows the results of expression of BMCC1 gene, PRUNE2 gene, and DD3 gene in a prostate cancer cell line as examined by semiquantitative RT-PCR.

The results of expression of BMCC1 gene, PRUNE2 gene, and DD3 gene in a prostate cancer cell line as examined by a semiquantitative RT-PCR are shown in FIG. 4. As a result, DD3 was confirmed to be highly expressed in androgen dependent LNCaP cells. Interestingly, it was elucidated that BMCC1 was highly expressed in LNCaP cells as well, while BMCC1 expression was reduced in PC3 cells and Du145 cells, which may correspond to prostate cancer with higher malignancy. These results suggest that BMCC1 gene expression is suppressively regulated as prostate cancer progresses.

Example 4

An Effect of Suppression of DD3 Expression by siRNA for DD3 on BMCC1 Gene Expression In order to examine an effect of suppression of DD3 expression by siRNA for DD3 on BMCC1 gene expression, a semiquantitative RT-PCR was carried out using a total RNA extracted from prostate cancer cell lines (an LNCaP cell line and a PC3 cell line) into which siRNA was introduced.

Figure 5:
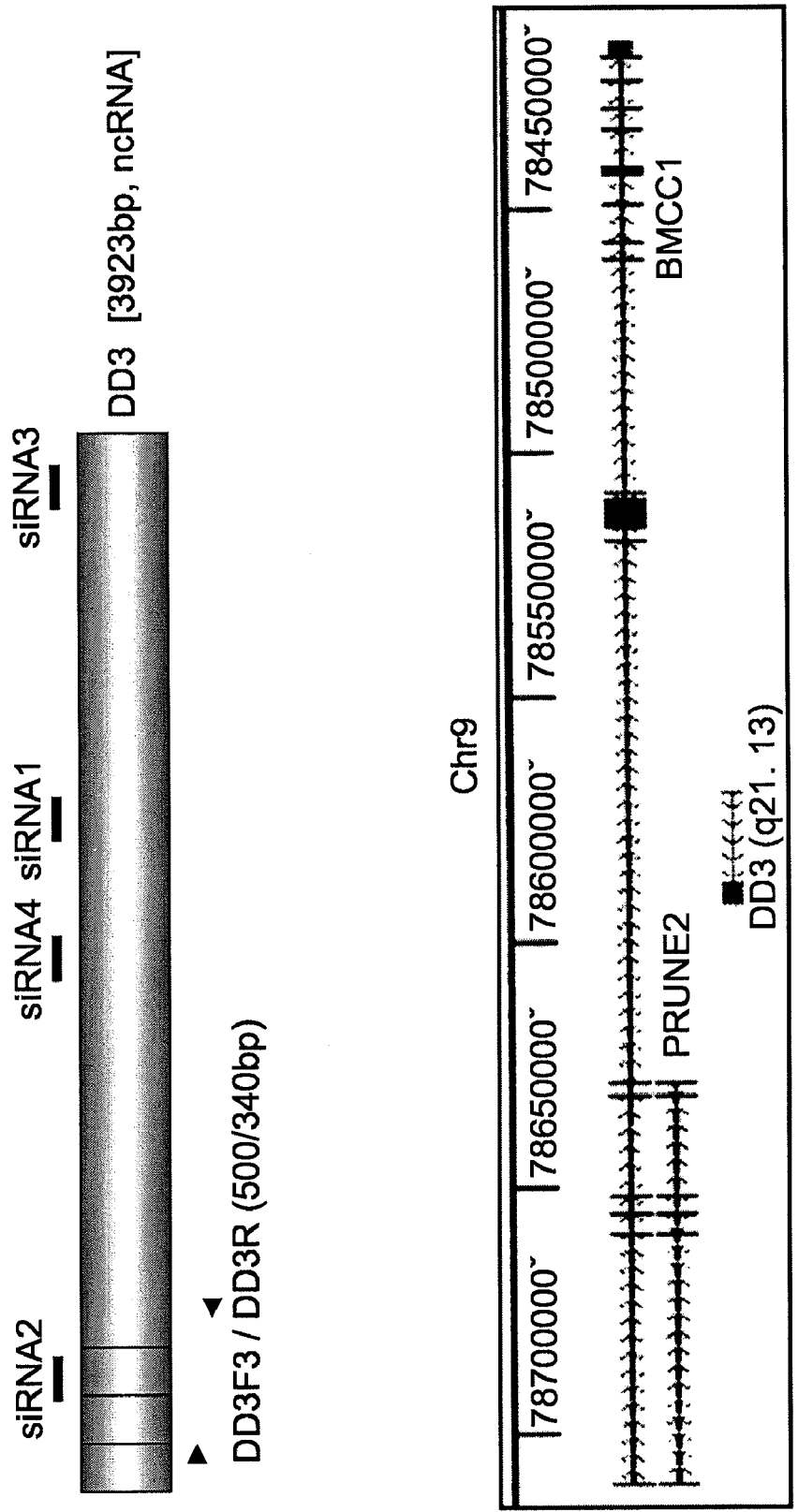
FIG. 5 schematically shows a structure of DD3 non-coding RNA (i.e., ncRNA) and a location of siRNA with respect to DD3.

Three kinds of siRNA for DD3 were designed and purchased from Integrated DNA Technologies, Inc. A structure of DD3 ncRNA and locations of siRNA for DD3 are shown schematically in FIG. 5. Sequences of the three kinds of siRNA to DD3 (i.e., DD3 siRNA 1, 2, and 3) are as follows;

```
DD3
siRNA1:
5'-ggaaccaagauacaaagaacucuga-3'           (SEQ ID NO: 11)
and

5'-ucagaguucuuuguaucuugguuccuu-3'         (SEQ ID NO: 12)

DD3
siRNA2:
5'-ucacuagaaacagcaagaugacaat-3'           (SEQ ID NO: 13)
and

5'-auugucaucuugcuguuucuagugaug-3'         (SEQ ID NO: 14)

DD3
siRNA3:
5'-ggcauacuauaucaacuuugauuct-3'           (SEQ ID NO: 15)
and

5'-agaaucaaaguugauauaguaugccaa-3'         (SEQ ID NO: 16)

control siRNA:
sense strand
5'-cuuccucucuuucucucccuuguga-3'           (SEQ ID NO: 17)
and antisense strand
5'-ucacaagggagagaaagagaggaagga-3'         (SEQ ID NO: 18)
```

HiPerfect, a product of QIAGEN, was used for transduction of siRNA. Cultured cells of each cell line were transduced with 5 nM of each siRNA according to a protocol of the product. The cultured cells were collected 48 hours after transduction and a total RNA was purified according to a protocol of the product. The methods described in Examples 1 to 4 were used for cDNA synthesis and PCR reactions except that, as a primer for detecting DD3, a DD3 (F3/R) primer set (SEQ ID NOS: 4 and 10) was used in FIG. 6, and a DD3 (taqF4/taqR2) primer set (SEQ ID NOS: 21 and 22) was used in FIG. 7. As a primer for detecting BMCC1, a BMCC1 (BNF2/BNR2) primer set (SEQ ID NOS: 1 and 2) was used, and as a primer for detecting PRUNE2, a PRUNE2 (BNF2/PRUNE2R1) primer set (SEQ ID NOS: 1 and 3) was used, and as a primer for detecting GAPDH1, a GAPDH1 (F/R) primer set (SEQ ID NOS: 6 and 7) was used.

<DD3 (taqF4/taqR2) Primers and PCR Reaction Conditions>

```
DD3;
taqF4:
5'-cacagagatccctgggagaaat-3'              (SEQ ID NO: 21)
and taqR2:
5'-ctgcccatcctttaaggaacac-3'              (SEQ ID NO: 22)
```

<A Composition of Reaction Solution>

| | |
|---|---|
| cDNA | 1 μl |
| 10x LA-Taq Buffer | 1 μl |
| 2.5 mM dNTPs | 1 μl |
| 2.5 mM MgCl$_2$ | 1 μl |
| Forward primers (10 μM) | 0.5 μl |
| Reverse primers (10 μM) | 0.5 μl |
| Sterilized water | 5 μl |
| LA-Taq | 0.1 μl |
| Total volume | 10 μl |

To carry out a PCR reaction using a DD3 (taqF4/taqR2) primer set, a tube containing a reaction solution of the above composition containing LA-Taq (product of Takara Bio Inc.) was set in a thermal cycler (Gene Amp® PCR System 9700, product of Applied Biosystems) and heated to 95° C. for 2 minutes. After that, a cycle containing 95° C. for 15 seconds→60° C. for 15 seconds→72° C. for 20 seconds was repeated 35 times, and the sample was kept at 72° C. for 7 minutes.

Figure 6:
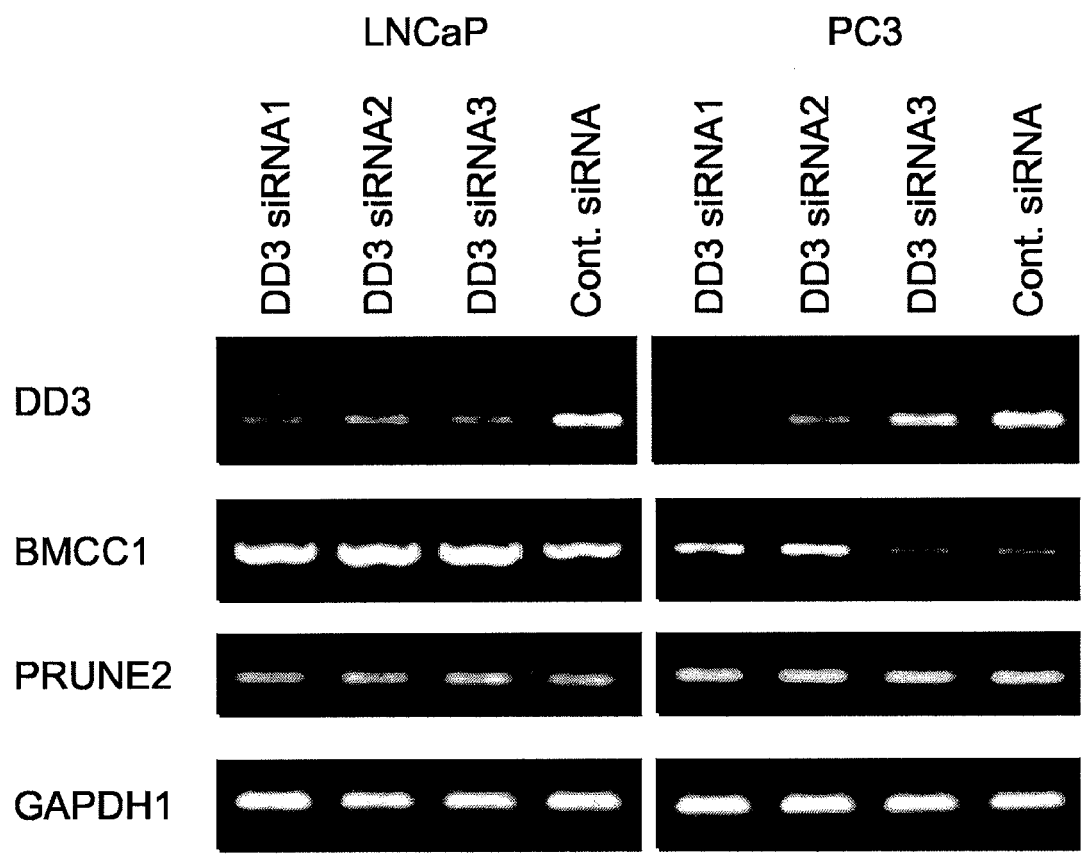
FIG. 6 shows the results of expression of BMCC1 gene, PRUNE2 gene, and DD3 gene in a prostate cancer cell line into which siRNA for DD3 was introduced as examined by semiquantitative RT-PCR.

The results of expression of BMCC1 gene, PRUNE2 gene, and DD3 gene in a prostate cancer cell line into which siRNA for DD3 was introduced as examined by a semiquantitative RT-PCR are shown in FIGS. 6 and 7. As a result, any of the siRNA was confirmed to inhibit DD3 expression (FIGS. 6 and 7). It was elucidated that in cells in which DD3 expression was inhibited, BMCC1 expression was enhanced in both of the LNCaP cells and the PC3 cells regardless of androgen dependency (FIG. 6).

Example 5

Preparation of an Anti-BMCC1 Antibody

An anti-BMCC1 antibody was prepared following the below-described procedures by using residues from 2074 to 2093 of BMCC1 protein (i.e., amino acid sequence: AKKPFSLKADGENPDILTHC, as shown by single-letter codes of amino acids; SEQ ID NO: 23; synthetic peptide by Medical & Biological Laboratories CO., LTD.) as an antigenic peptide.

A rabbit (Japanese white rabbit) was immunized with the antigenic peptide, and a booster immunization was given. After the eighth immunization, whole blood was collected and an antibody component which specifically recognized the antigenic peptide was purified using a column in which antigenic peptide was solid-phased. Specificity of the antibody was confirmed by an ELISA analysis using the antigenic peptide. The antibody component thus obtained was used as an anti-BMCC1 antibody in the following experiment.

Example 6

Figure 8:
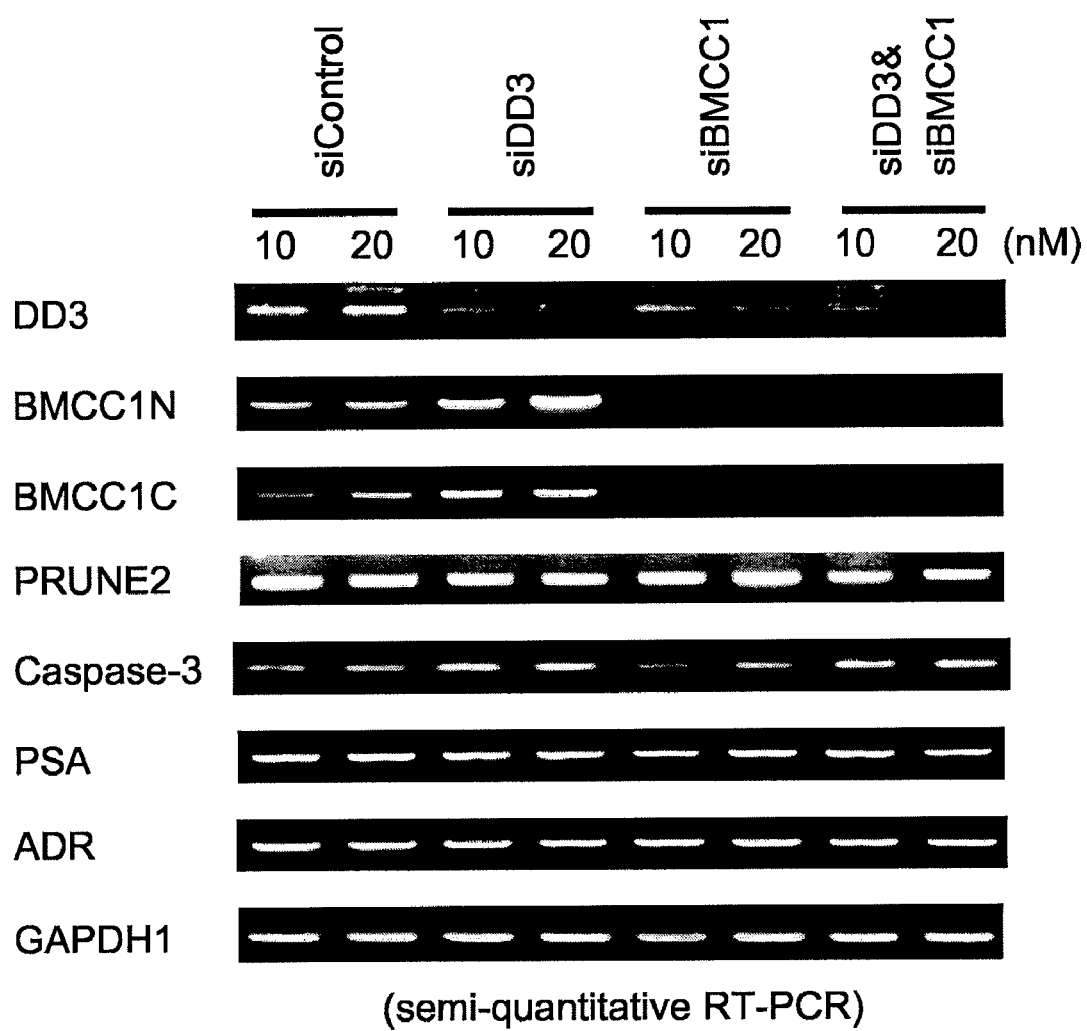
FIG. 8 shows the results of expression of BMCC1 gene, PRUNE2 gene, and DD3 gene in LNCaP cells into which siRNA for DD3 was introduced as examined by semiquantitative RT-PCR.

An Effect of Suppression of DD3 Expression on BMCC1 Protein Expression and Cell Viability In a similar manner to Example 5, siRNA was introduced into human prostate cancer cell line LNCaP by a lipofection method (HiPerfect, product of QIAGEN), and the cells were cultured for 48 hours. A total RNA extracted from the cultured cells was used for cDNA synthesis, and semiquantitative RT-PCR was carried out (FIG. 8).

As siRNA for BMCC1, the siRNA having the following sequence was designed and purchased from Integrated DNA Technologies, Inc.

```
siBMCC1-1:
5'-ggagaaggauauugacuugaagctg-3'     (SEQ ID NO: 24)
and

5'-cagcuucaagucaauauccuuucuccau-3'  (SEQ ID NO: 25)

siBMCC1-2:
5'-ggaguaucaggaagcaaaucaggta-3'     (SEQ ID NO: 26)
and

5'-uaccugauuugcuuccugauacuccaa-3'   (SEQ ID NO: 27)

siBMCC1-3:
5'-cccagugagauaaacaaugaagcag-3'     (SEQ ID NO: 28)
and

5'-cugcuucauuguuuaucucacugggug-3'   (SEQ ID NO: 29)
```

Also, DD3 siRNA1 (SEQ ID NOS: 11 and 12), DD3 siRNA3 (SEQ ID NOS: 15 and 16) and DD3 siRNA4 (SEQ ID NOS: 30 and 31) was used as siRNA for DD3.

```
DD3 siRNA4:
5'-ggaguuagauuuaugcauauugugguu-3'   (SEQ ID NO: 30)
and

5'-ccacaauaugcauaaaucuaacucc-3'     (SEQ ID NO: 31)
```

A DD3 (F3/R) primer set (SEQ ID NOS: 4 and 10) was used as a primer for detecting DD3, A BMCC1N (BNF2/BNR2) primer set (SEQ ID NOS: 1 and 2) and a BMCC1C (kiaa0367F/R) primer set (SEQ ID NOS: 8 and 9) were used as primers for detecting BMCC1, a PRUNE2 (BNF2/PRUNE2R1) primer set (SEQ ID NOS: 1 and 3) was used as a primer for detecting PRUNE2, a Caspase-3 (F/R) primer set (refer to Patent Document 1) was used as a primer for detecting Caspase-3, a PSA (F/R) primer set (SEQ ID NOS: 32 and 33) was used as a primer for detecting PSA, an ADR (F/R) primer set (SEQ ID NOS: 34 and 35) was used as a primer for detecting ADR, and a GAPDH1 (F/R) primer set (SEQ ID NOS: 6 and 7) was used as a primer for detecting GAPDH1.

<PSA (F/R) Primer and ADR (F/R) Primer>

```
PSA;
F: 5'-gcctctcgtggcagggcagt-3'       (SEQ ID NO: 32)
and

R: 5'-gggtgaacttgcgcacacac-3'       (SEQ ID NO: 33)

ADR;
F: 5'-tcaaaagagccgctgaagggaaaca-3'  (SEQ ID NO: 34)
and

R: 5'-acaccatgagccccatccaggagta-3'  (SEQ ID NO: 35)
```

Figure 9:
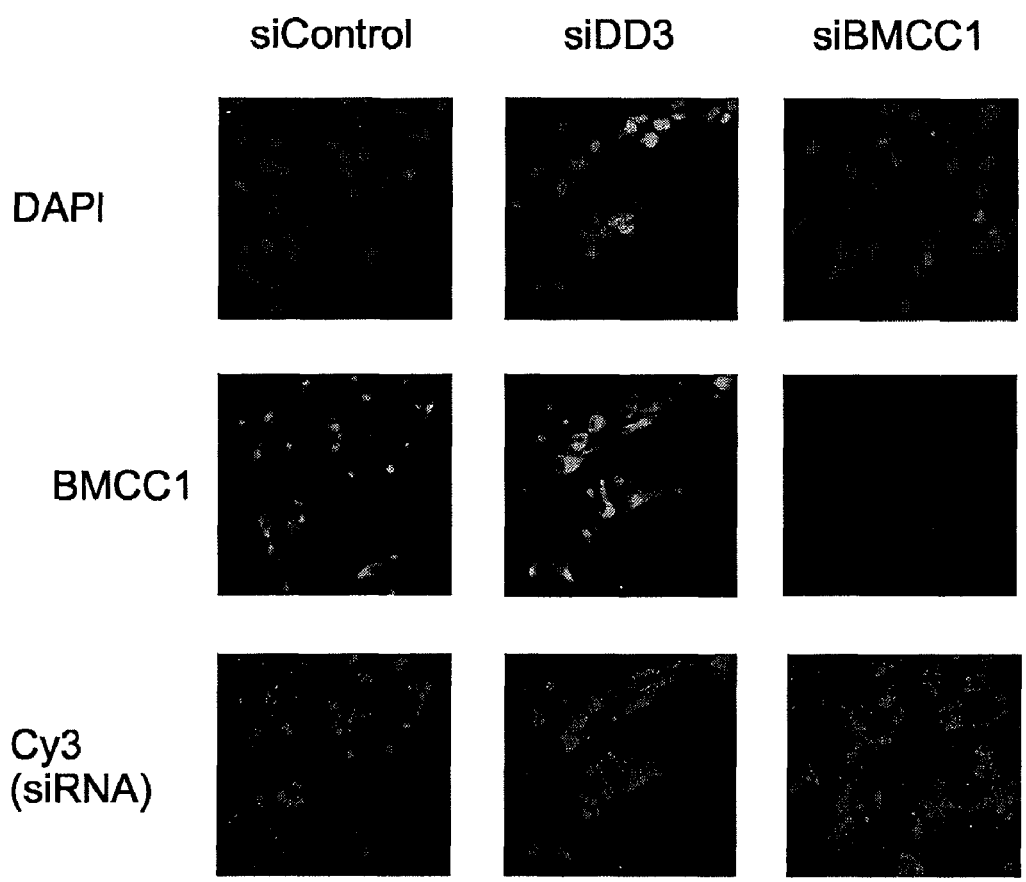
FIG. 9 is an immunostaining image of BMCC1 protein in LNCaP cells 48 hours after introduction of siRNA.
Figure 10:
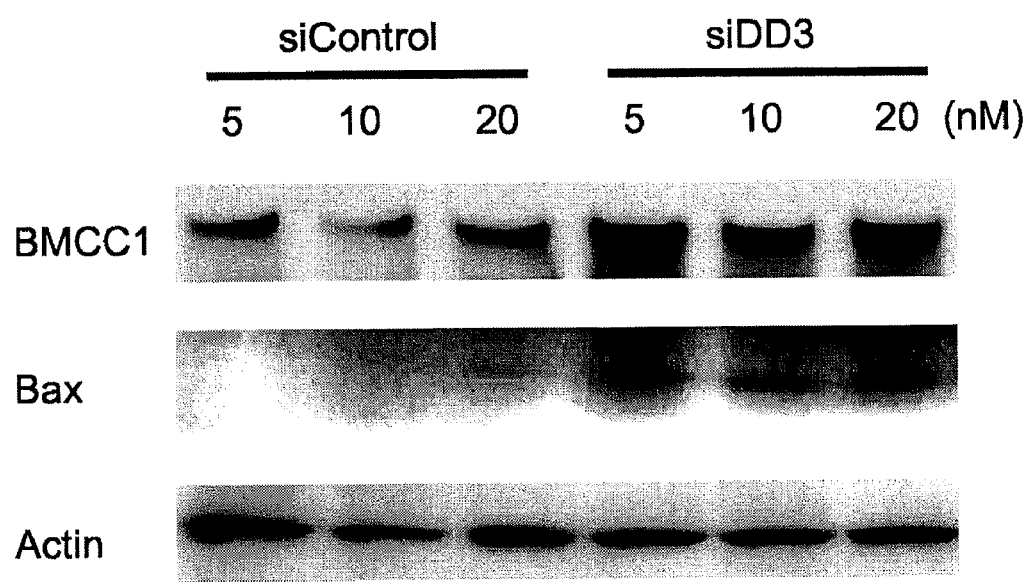
FIG. 10 is a Western blot image of BMCC1 protein in LNCaP cells into which siRNA for DD3 was introduced.

BMCC1 protein expression in cells in which DD3 expression or BMCC1 expression was suppressed was then confirmed by immunostaining and Western blotting using the anti-BMCC1 antibody (FIGS. 9 and 10). Procedures of the immunostaining are as follows. Cells which were left for 48 hours after introduction of siRNA were fixed with 10% formalin for 15 minutes at room temperature, and treated with PBS containing 0.1% TritonX for 10 minutes at room temperature. After that, the cells were treated with the anti-BMCC1 antibody (1/500 dilution) for 3 hours at room temperature, and then with an anti-rabbit antibody labeled with Alexa488 (product of Molecular Probes, Inc., 1/1000 dilution) for 2 hours at room temperature. The cells in which nuclei were stained with DAPI were observed under a confocal laser microscope (product of Leica Microsystems). An immunostaining image of BMCC1 protein in the LNCaP cells 48 hours after introduction of siRNA is shown in FIG. 9 (nuclei: blue, BMCC1: green, Cy3-siRNA: red).

Procedures of the Western blot are as follows. A total extraction solution of the cells which were left for 48 hours after introduction of siRNA was separated by a SDS-page and transferred to a PVDF membrane (product of Millipore Corporation), followed by treatment with the anti-BMCC1 antibody (1/500 dilution) for 3 hours at room temperature and with an anti-rabbit antibody labeled with HRP (product of Zymed Laboratories, Inc., 1/1500 dilution) for 2 hours at room temperature. The membrane was subjected to color development using ECL (product of GE Healthcare), and exposed to an X-ray film (product of Fujifilm Corporation) for detection. A Western blot image of BMCC1 protein in the LNCaP cells into which siRNA for DD3 was introduced is shown in FIG. 10.

Figure 11:
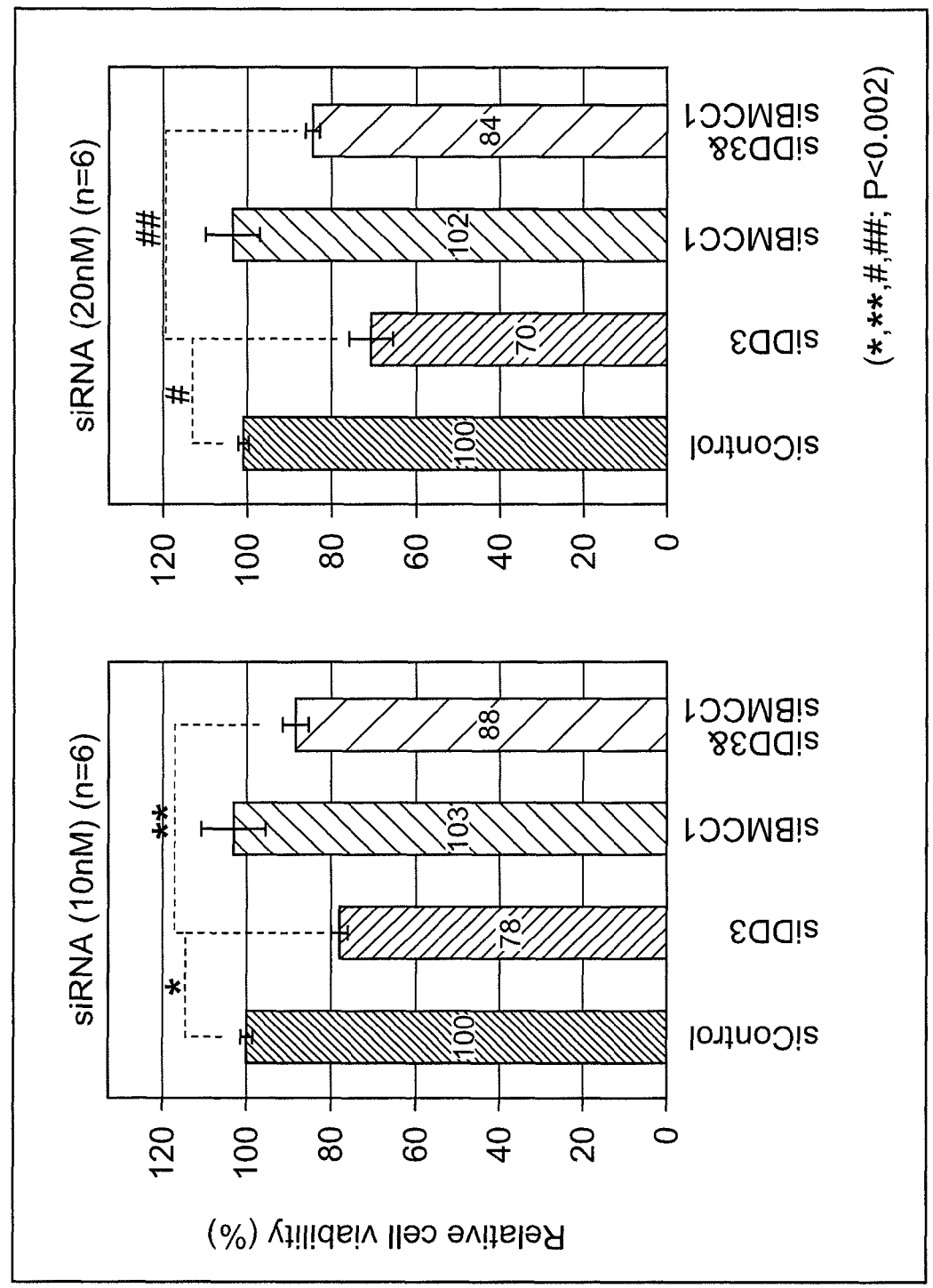
FIG. 11 shows a relative cell viability rate of LNCaP cells 48 hours after introduction of siRNA.

Furthermore, using a WST-8 kit (product of Dojindo Molecular Technologies, Inc.), viability of the cells which were left for 48 hours after introduction of siRNA was measured following a manual thereof. Viability of the cells 48 hours after introduction of siRNA is shown in FIG. 11.

As a result, enhanced BMCC1 expression was confirmed in the LNCaP cells in which DD3 expression was suppressed by RT-PCR (FIG. 8). In addition to an analysis at the mRNA level, BMCC1 expression was confirmed to be enhanced at the protein level as well by immunostaining and Western blotting using the anti-BMCC1 antibody (FIGS. 9 and 10). Furthermore, it was confirmed that cell viability was suppressed in the LNCaP cells in which DD3 expression was suppressed (FIG. 11).

Example 7

Figure 12:
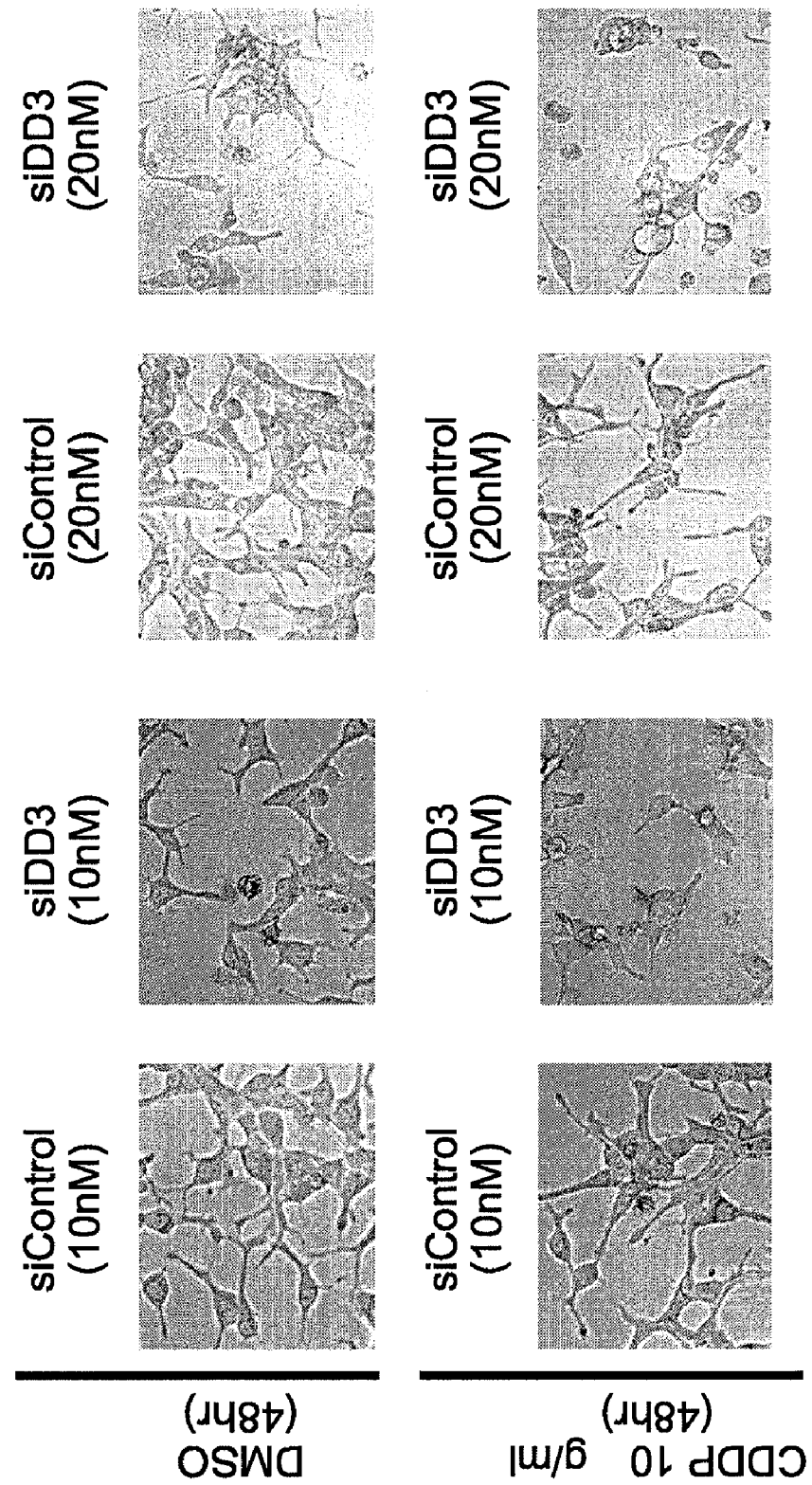
FIG. 12 shows LNCaP cells 48 hours after introduction of siRNA in the presence of cisplatin.
Figure 13:
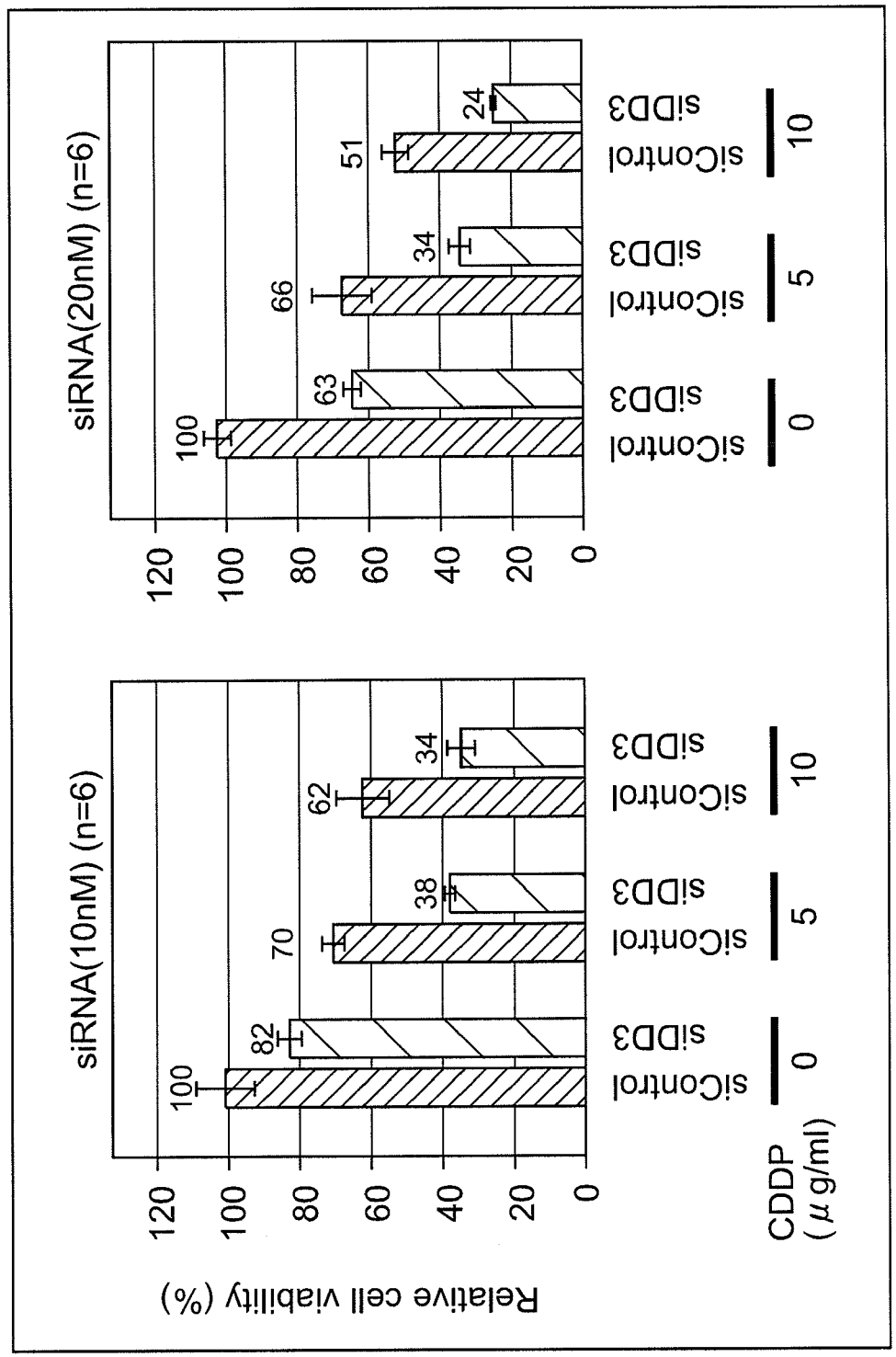
FIG. 13 shows a relative cell viability rate of LNCaP cells 48 hours after introduction of siRNA in the presence of cisplatin.
Figure 14:
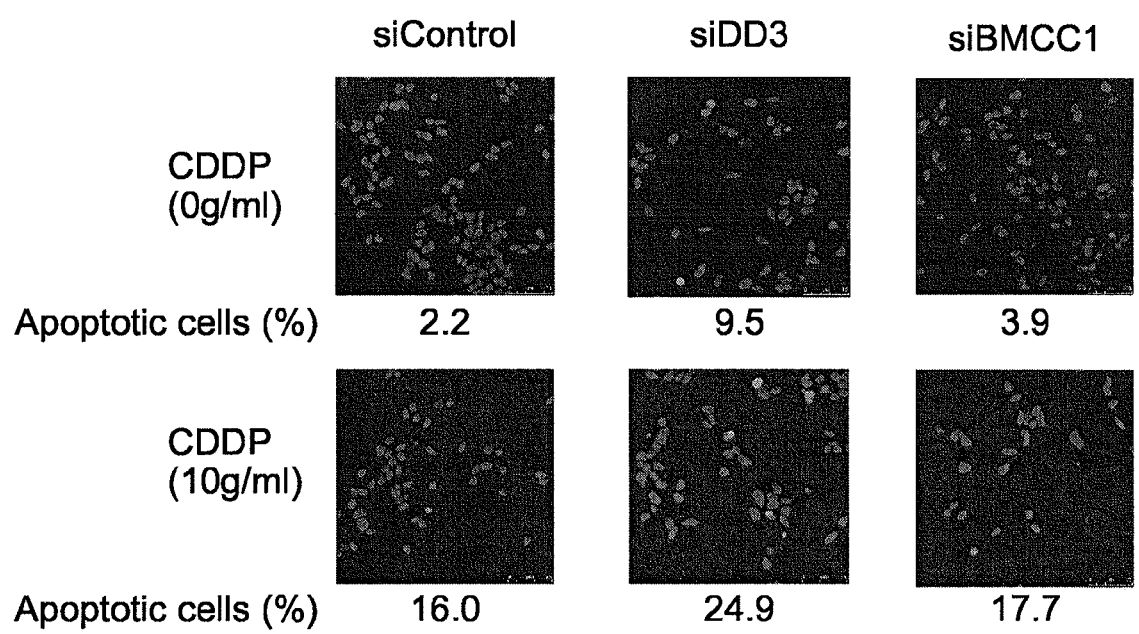
FIG. 14 shows apoptotic cells 48 hours after introduction of siRNA in the presence of cisplatin.

An Effect of Inhibition of DD3 Expression on Prostate Cancer Cells in the Presence of an Anti-Cancer Agent, Cisplatin An effect of inhibition of DD3 expression on prostate cancer cells in the presence of cisplatin was examined by the below-described method. LNCaP cells into which siRNA for DD3 was introduced were treated with DMSO (product of Nacalai Tesque, Inc.) or cisplatin, CDDP (product of SIGMA Corporation) for 48 hours, and observed under a microscope (product of Leica Microsystems) (FIG. 12). Also, viability of the cells 48 hours after siRNA introduction was measured using a WST-8 kit (FIG. 13). Apoptotic cells were detected by a TUNEL assay kit (product of F. Hoffman—La Roche, Ltd.) following a manual thereof, and quantified by observation under a confocal laser microscope (product of Leica Microsystems). The results of detection of apoptotic cells in the LNCaP cells 48 hours after siRNA introduction are shown in FIG. 14 (nuclei: blue, and apoptotic cells: red). Ratios of apoptotic cells/nuclei were determined for about 400 cells for each condition and were described as the ratio (%) at the bottom of each picture of FIG. 14.

As a result, it was elucidated that a sensitivity of the LNCaP cells in which DD3 expression was suppressed to an anti-cancer agent, cisplatin, was increased (FIGS. 12 to 14). That is, effects of suppressing viability (FIGS. 12 and 13) and promoting apoptosis (FIG. 14) of prostate cancer cells by cisplatin were enhanced additively and/or synergistically by suppressing DD3 expression.

Example 8

Figure 15:
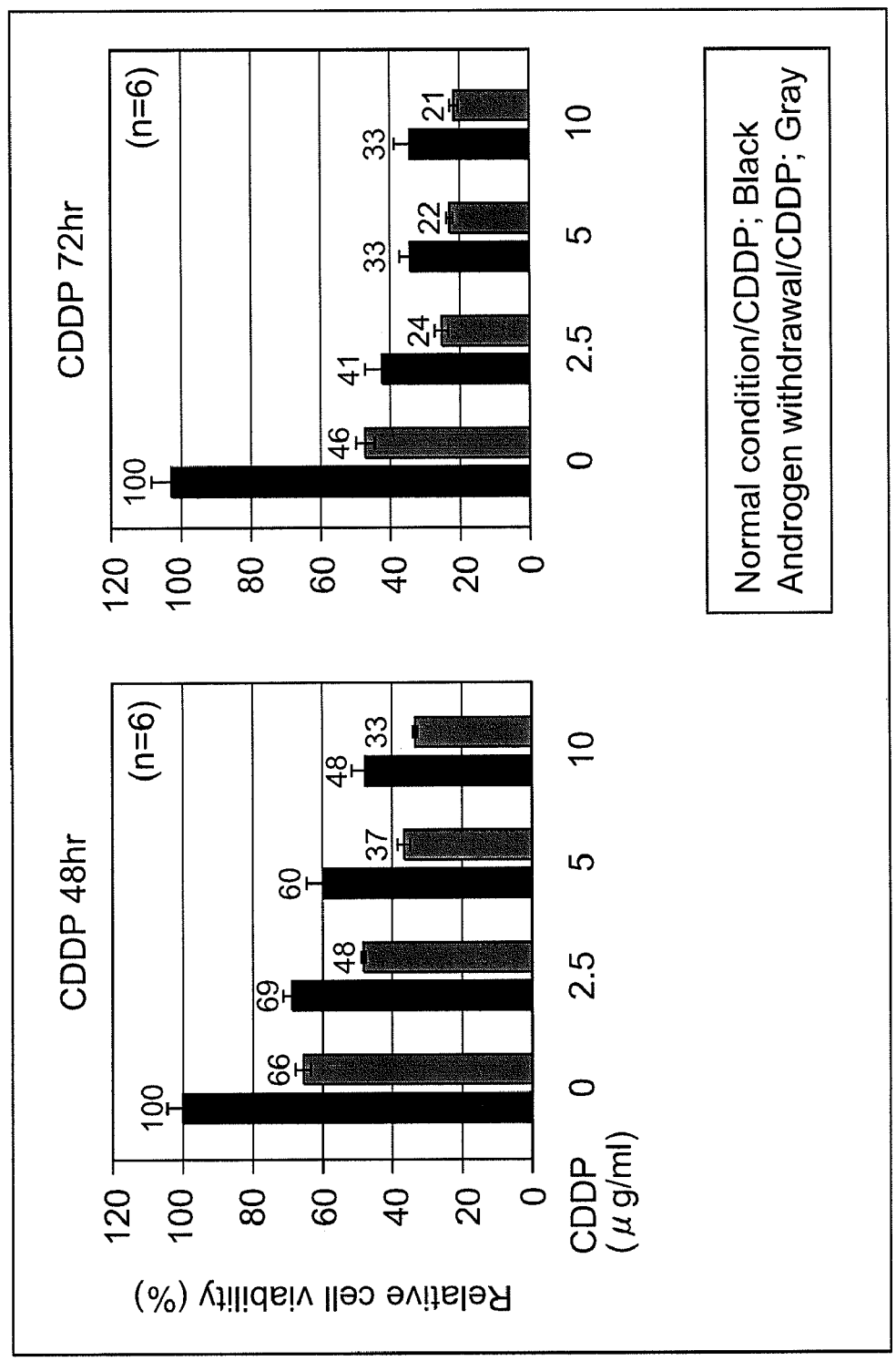
FIG. 15 shows a relative cell viability rate of LNCaP cells in the presence of cisplatin.
Figure 16:
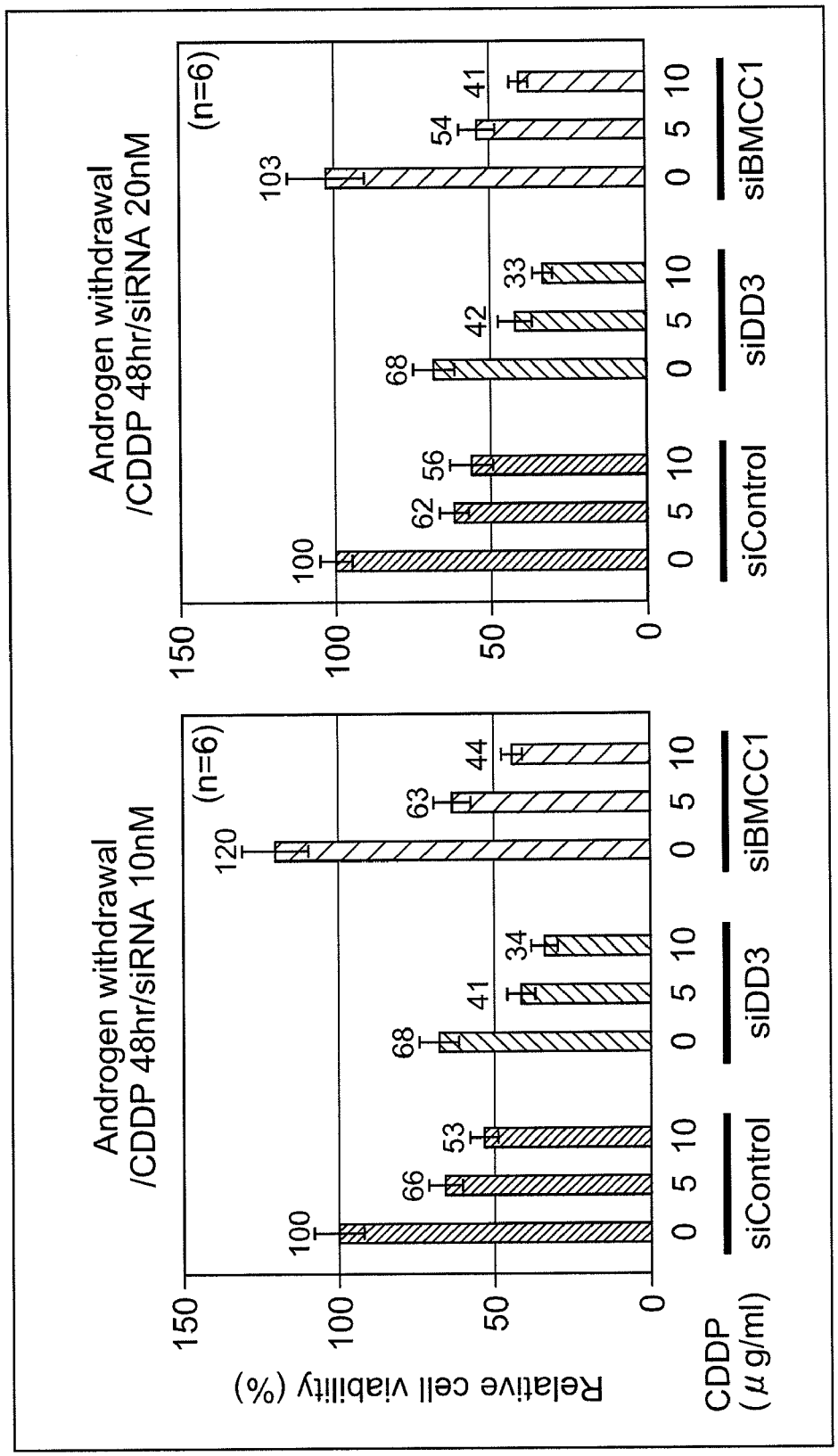
FIG. 16 shows a relative cell viability rate of LNCaP cells 48 hours after introduction of siRNA in the presence of cisplatin.

An Effect of Suppression of DD3 Expression on Prostate Cancer Cells in the Absence of Androgen It is known that androgen blockade therapy is effective for early-stage prostate cancer because most of the early-stage prostate cancer is androgen dependent. Also, viability of LNCaP cells is suppressed in the absence of androgen. In view of the foregoing, effects of suppression of DD3 expression and treatment with cisplatin on prostate cancer cells in the absence of androgen were examined following the below-described method. LNCaP cells were treated with DMSO or CDDP for 48, 72 hours in RPMI media containing 5% FBS containing androgen at a low concentration (product of Invitrogen Corporation), and viability of the cells was measured using a WST-8 kit (FIG. 15). Then, LNCaP cells into which siRNA was introduced were treated with DMSO or CDDP (product of SIGMA Corporation) for 48 hours in RPMI media containing 5% FBS containing androgen at a low concentration, and viability of the cells was measured using a WST-8 kit (FIG. 16).

As a result, an effect of suppressing viability of the LNCaP cells in the absence of androgen was further enhanced by treatment with cisplatin (FIG. 15). Prostate cancer treatment using hormone therapy in combination with an anti-cancer agent is clinically practiced. Interestingly, it was elucidated that by treating the LNCaP cells in which DD3 expression was suppressed with cisplatin in the absence of androgen, viability of the cells was suppressed synergistically (FIG. 16). Also, an effect of suppressing viability of the LNCaP cells in the absence of androgen was further enhanced by suppression of DD3 expression (FIG. 16, data for non-addition of CDDP). Accordingly, from the results of Examples 7 and 8, viability of cells was found to be suppressed more effectively by employing treatment with cisplatin and/or removal of androgen concurrently in addition to suppression of DD3 expression. This result correlates with findings that BMCC1 expression was increased with either treatment with cisplatin or removal of androgen, in addition to suppression of DD3 expression. On the contrary, it was found that suppression of viability of cells was released, although partially, in the cells in which BMCC1 expression was suppressed in addition to suppression of DD3 expression (FIG. 11). Accordingly, suppression of DD3 expression and combination use thereof with another treatment method are considered effective as novel treatment methods for prostate cancer.

In view of the foregoing, a possibility that DD3 suppressed BMCC1 gene expression and promoted cancer progression was strongly suggested based on a finding that DD3 expression was enhanced in androgen-dependent cancer cells, which corresponded to early-stage prostate cancer, while BMCC1 gene expression was suppressively regulated as prostate cancer progressed (FIG. 4) and a finding that BMCC1 gene expression was enhanced by suppression of DD3 expression (FIGS. 6 and 7). Because BMCC1 has a function to promote apoptosis and acts as a cancer suppressor gene on one side, a method found by Examples of the present application, which directs to recovering BMCC1 expression by suppression of DD3 expression by siRNA, is considered effective for cancer treatment. In fact, based on that BMCC1 expression was enhanced at the mRNA level and the protein level by suppression of DD3 expression (FIGS. 6 to 10) and that cell viability of prostate cancer cells was suppressed and apoptosis was promoted by suppression of DD3 expression (FIGS. 11 and 14), it was elucidated that suppression of DD3 expression enhanced BMCC1 gene expression and inhibited cancer progression. The above findings suggested that siRNA for DD3 was useful as a therapeutic agent for cancer. Also, based on the results from PC3 cells (FIG. 6), it is considered useful as a method for treatment of androgen independent prostate cancer, which is difficult to treat.

Furthermore, viability of cells was more effectively suppressed by employing treatment with cisplatin and/or removal of androgen concurrently in addition to suppression of DD3 expression (Examples 7 and 8). Accordingly, it was suggested that combination use of the therapeutic agent of the present invention with another treatment method such as an anti-cancer agent and androgen blockade therapy was effective.

What is claimed is:

1. A method for detecting cancer in a specimen suspected of cancer, comprising:
    measuring a level of BCH motif-containing molecule at the carboxyl terminal region 1 gene expression in the specimen suspected of cancer;
    comparing the level of BCH motif-containing molecule at the carboxyl terminal region 1 gene expression in the specimen suspected of cancer with a level of BCH motif-containing molecule at the carboxyl terminal region 1 gene expression in a normal specimen and a level of BCH motif-containing molecule at the carboxyl terminal region 1 gene expression in a cancer specimen;
    comparing the level of Differential Display Code 3 gene expression in the specimen suspected of cancer with a level of Differential Display Code 3 gene expression in a normal specimen and a level of Differential Display Code 3 gene expression in a cancer specimen; and
    determining the specimen suspected of cancer is cancerous when:
        the level of BCH motif-containing molecule at the carboxyl terminal region 1 gene expression in the specimen suspected of cancer is either (i) lower than the level of BCH motif-containing molecule at the carboxyl terminal region 1 gene expression in the normal specimen, (ii) the same level as the level of BCH motif-containing molecule at the carboxyl terminal region 1 gene expression in the cancer specimen, or, both (i) and (ii); and
        the level of Differential Display Code 3 gene expression in the specimen suspected of cancer is either (i) higher than the level of Differential Display Code 3 gene expression in the normal specimen, (ii) the same level as the level of Differential Display Code 3 gene expression in the cancer specimen, or, both (i) and (ii);
    wherein the cancer is prostate cancer.

2. The method according to claim 1, wherein the specimen is a cell or a piece of tissue.

* * * * *